(12) United States Patent
Bitton et al.

(10) Patent No.: US 11,833,333 B2
(45) Date of Patent: Dec. 5, 2023

(54) DRUG TRACKING DEVICE

(71) Applicants: INSULINE MEDICAL LTD., Jerusalem (IL); Gabriel Bitton, Jerusalem (IL); Ephraim Oved, Kiryat-Gat (IL); Avi Ben-Simon, Zichron-Yaakov (IL)

(72) Inventors: Gabriel Bitton, Jerusalem (IL); Ephraim Oved, Kiryat-Gat (IL); Avi Ben-Simon, Zichron-Yaakov (IL)

(73) Assignee: Insuline Medical LTD, Jerusalem (IL)

( * ) Notice: Subject to any disclaimer, the term of this patent is extended or adjusted under 35 U.S.C. 154(b) by 303 days.

(21) Appl. No.: 16/629,965

(22) PCT Filed: Jul. 12, 2018

(86) PCT No.: PCT/IB2018/055157
§ 371 (c)(1),
(2) Date: Jan. 10, 2020

(87) PCT Pub. No.: WO2019/012475
PCT Pub. Date: Jan. 17, 2019

(65) Prior Publication Data
US 2021/0085876 A1    Mar. 25, 2021

Related U.S. Application Data

(60) Provisional application No. 62/630,742, filed on Feb. 14, 2018, provisional application No. 62/613,025, (Continued)

(51) Int. Cl.
*A61M 5/31*     (2006.01)

(52) U.S. Cl.
CPC ....... *A61M 5/31* (2013.01); *A61M 2005/3126* (2013.01); *A61M 2205/3306* (2013.01); *A61M 2205/52* (2013.01)

(58) Field of Classification Search
CPC ............ A61M 5/31; A61M 2005/3126; A61M 2205/3306; A61M 2205/52;
(Continued)

(56) References Cited

U.S. PATENT DOCUMENTS

| 4,359,719 A | 11/1982 | Schwarzer |
| 5,363,842 A | 11/1994 | Mishelevich et al. |

(Continued)

FOREIGN PATENT DOCUMENTS

| CN | 102824669 | 12/2012 |
| EP | 2182456 | 5/2010 |

(Continued)

*Primary Examiner* — Lauren P Farrar

(57) ABSTRACT

A drug tracking device used in combination with a drug injection device. The drug tracking device may comprise a housing configured to engage with the drug injection device, an optical sensor configured to capture an image of a portion of the drug injection device. The portion of the drug injection device displays indicia of drug doses, such that a captured image includes at least one indicia of a drug dose. The drug tracking device may include a memory module having pre-stored indicia of drug doses, and a processor having instructions operating thereon configured to cause the processor to determine an injected drug dose by comparing at least one indicia of the drug dose in the captured image with the pre-stored indicia of drug doses.

18 Claims, 18 Drawing Sheets

Related U.S. Application Data filed on Jan. 2, 2018, provisional application No. 62/531,377, filed on Jul. 12, 2017.

(58) Field of Classification Search
CPC ...... A61M 2005/3125; A61M 2205/18; A61M 2205/3317; A61M 2205/3368; A61M 2205/3375; A61M 2205/3569; A61M 2205/502; A61M 2205/583; A61M 2205/584; A61M 2205/587; A61M 2209/00; A61M 5/315; A61M 5/20; G01F 11/021; G16H 20/17; G16H 40/63

See application file for complete search history.

(56) References Cited

U.S. PATENT DOCUMENTS

| | | |
|---|---|---|
| 5,536,249 A | 7/1996 | Castellano et al. |
| 6,514,230 B1 | 2/2003 | Munk et al. |
| 8,038,629 B2 | 10/2011 | Solanki et al. |
| 8,409,133 B2 | 4/2013 | Pesach et al. |
| 8,827,979 B2 | 9/2014 | Pesach et al. |
| 9,067,022 B2 | 6/2015 | Baek et al. |
| 9,220,837 B2 | 12/2015 | Pesach et al. |
| 9,526,826 B2 | 12/2016 | Nagar et al. |
| 2004/0152979 A1 | 8/2004 | Sakakibara et al. |
| 2005/0182358 A1 | 8/2005 | Veit et al. |
| 2008/0312604 A1 | 12/2008 | Boesen |
| 2009/0051560 A1 | 2/2009 | Manning et al. |
| 2009/0069742 A1 | 3/2009 | Larsen |
| 2009/0076458 A1 | 3/2009 | Nielsen et al. |
| 2009/0256703 A1 | 10/2009 | Bolton |
| 2010/0069730 A1 | 3/2010 | Bergstrom et al. |
| 2010/0121170 A1 | 5/2010 | Rule |
| 2010/0286467 A1 | 11/2010 | Pesach et al. |
| 2010/0292557 A1 | 11/2010 | Pesach et al. |
| 2011/0295215 A1 | 12/2011 | Nielsen et al. |
| 2011/0313349 A1 | 12/2011 | Krulevitch et al. |
| 2012/0022458 A1 | 1/2012 | Oh et al. |
| 2012/0036018 A1 | 2/2012 | Feliciano et al. |
| 2012/0143021 A1 | 6/2012 | Nagar |
| 2012/0203164 A1 | 8/2012 | Bitton et al. |
| 2012/0233834 A1 | 9/2012 | Szechinski et al. |
| 2013/0197445 A1 | 8/2013 | Schabbach et al. |
| 2013/0236872 A1 | 9/2013 | Laurusonis et al. |
| 2013/0245545 A1 | 9/2013 | Arnold et al. |
| 2014/0194826 A1 | 7/2014 | Nielsen et al. |
| 2014/0207080 A1 | 7/2014 | Allerdings |
| 2014/0207099 A1 | 7/2014 | Nagar et al. |
| 2014/0213976 A1 | 7/2014 | Bitton et al. |
| 2014/0354998 A1 | 12/2014 | Bock et al. |
| 2015/0032059 A1 | 1/2015 | Allerdings et al. |
| 2015/0290396 A1 | 10/2015 | Nagar et al. |
| 2015/0314063 A1 | 11/2015 | Nagar et al. |
| 2016/0166777 A1 | 6/2016 | Bitton et al. |
| 2017/0368263 A1* | 12/2017 | Ploch ................ A61M 5/31551 |
| 2018/0268236 A1* | 9/2018 | Klemm ............ A61M 5/31525 |
| 2018/0280624 A1 | 10/2018 | Bitton et al. |
| 2020/0038600 A1 | 2/2020 | Bitton et al. |

FOREIGN PATENT DOCUMENTS

| | | |
|---|---|---|
| EP | 2296730 | 3/2011 |
| EP | 2451513 | 5/2012 |
| EP | 2692378 | 2/2014 |
| EP | 2926846 | 10/2015 |
| WO | 2007107564 | 9/2007 |
| WO | 2008051044 | 5/2008 |
| WO | 2008114218 | 9/2008 |
| WO | 200907600 | 1/2009 |
| WO | 201052579 | 5/2010 |
| WO | 2010132579 | 11/2010 |
| WO | 201132956 | 3/2011 |
| WO | 2011058268 | 5/2011 |
| WO | 2011117212 | 9/2011 |
| WO | 2012052335 | 4/2012 |
| WO | 2012153295 | 11/2012 |
| WO | 2013034716 | 3/2013 |
| WO | 2013050535 | 4/2013 |
| WO | 2013120770 | 8/2013 |
| WO | 2013120773 | 8/2013 |
| WO | 2013120774 | 8/2013 |
| WO | 2013120775 | 8/2013 |
| WO | 2013120776 | 8/2013 |
| WO | 2013120777 | 8/2013 |
| WO | 2013120778 | 8/2013 |
| WO | 2013138830 | 9/2013 |
| WO | 2014020008 | 2/2014 |
| WO | 2014020010 | 2/2014 |
| WO | 2014064691 | 5/2014 |
| WO | 2014111337 | 7/2014 |
| WO | 2014128155 | 8/2014 |
| WO | 2014152704 | 9/2014 |
| WO | 2014173767 | 10/2014 |
| WO | 2014173773 | 10/2014 |
| WO | 2015136513 | 9/2015 |
| WO | 201634552 | 3/2016 |

* cited by examiner

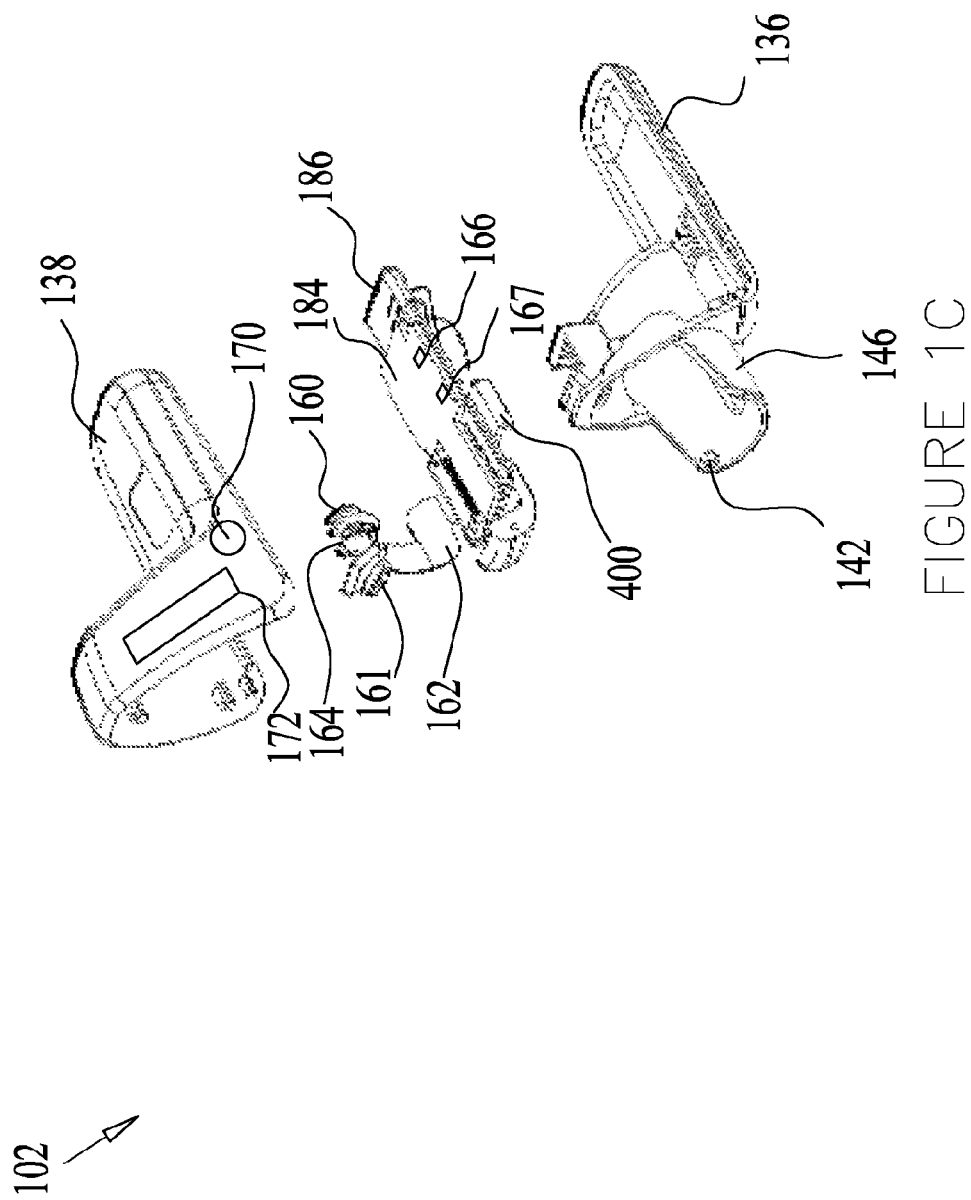

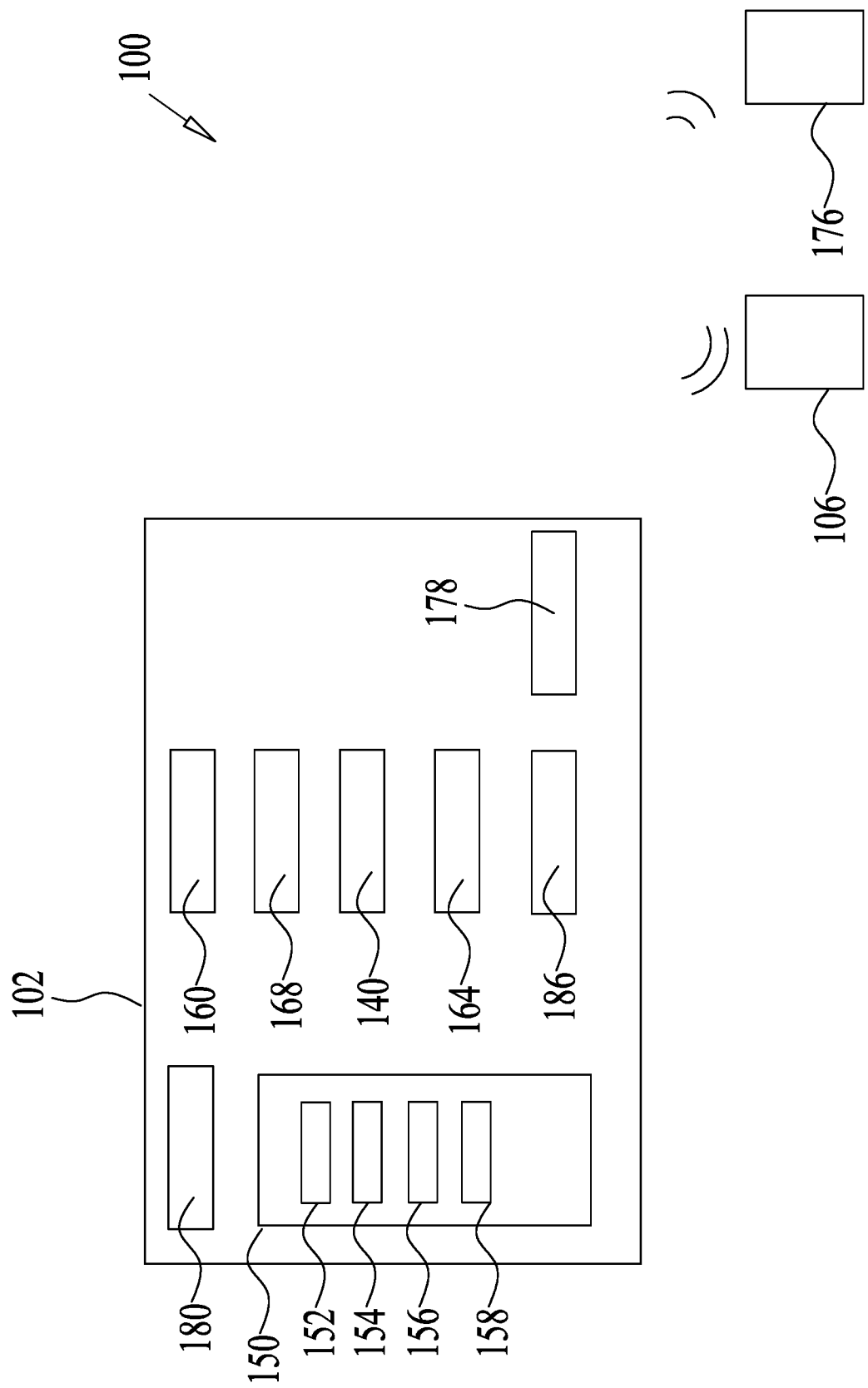

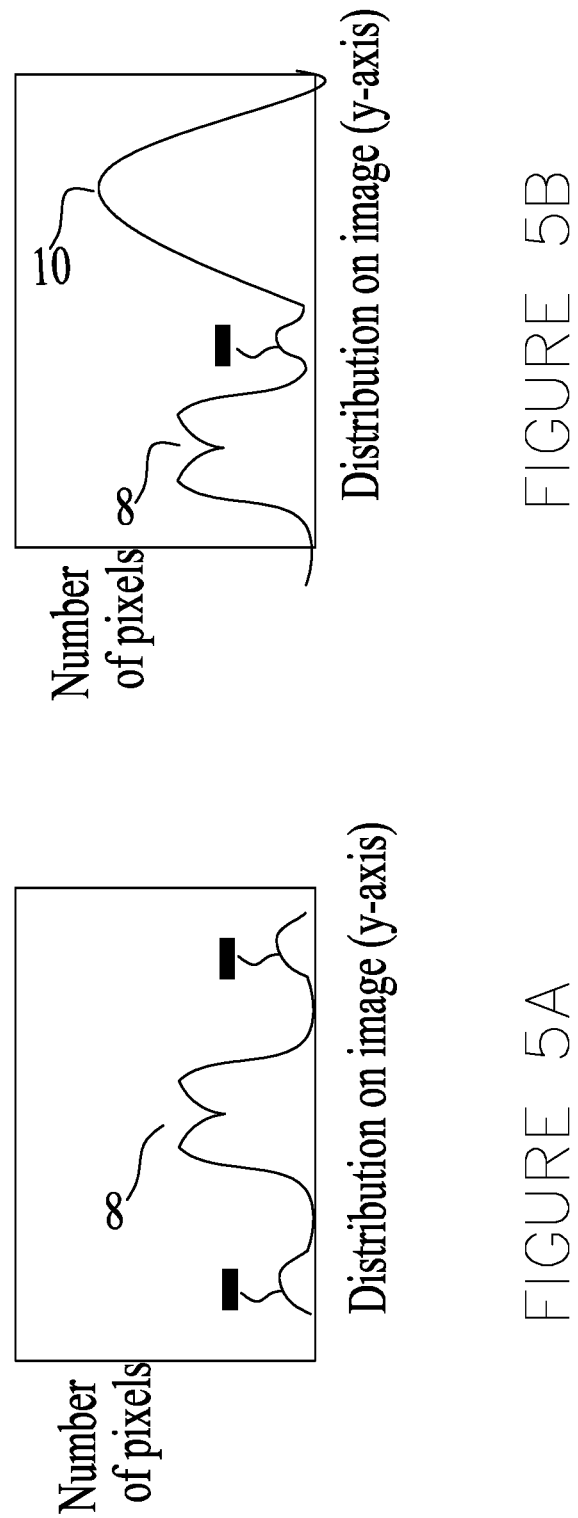

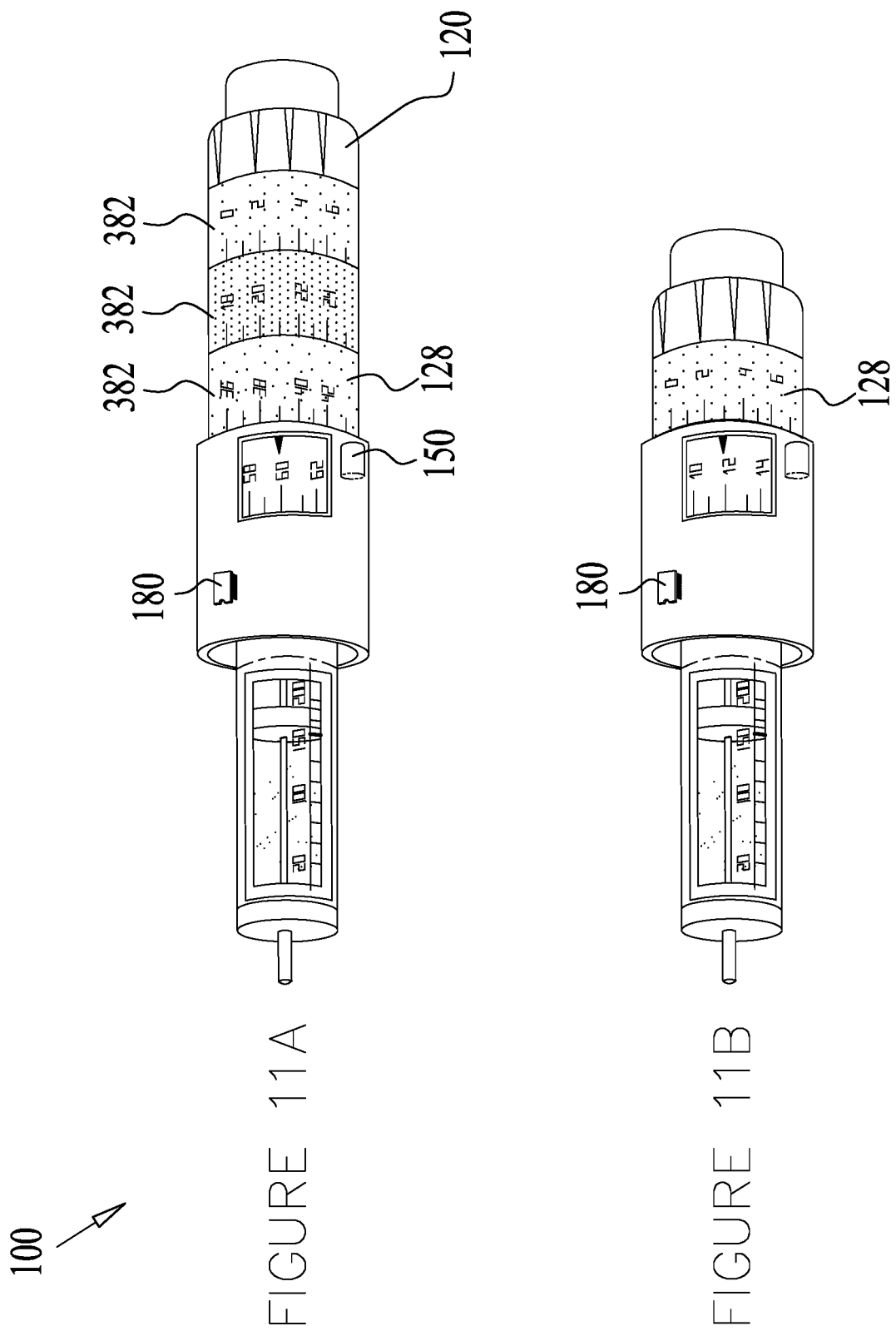

DRUG TRACKING DEVICE

CROSS REFERENCE TO RELATED APPLICATIONS

This application claims the benefit of International Patent Application No. PCT/IB2018/055157, filed Jul. 12, 2018 and entitled "Drug Tracking Device" which claims priority to U.S. Provisional Patent Application No. 62/531,377 filed Jul. 12, 2017, and entitled "Drug Tracking Device"; U.S. Provisional Patent Application No. 62/613,025, filed Jan. 2, 2018, and entitled "Drug Tracking Device"; and U.S. Provisional Patent Application No. 62/630,742, filed Feb. 14, 2018, and entitled "Drug Tracking Device". The disclosures of each of the above-referenced applications are hereby expressly incorporated by reference in their entireties.

TECHNICAL FIELD

Embodiments of the present disclosure generally relate to drug dispensers and tracking devices used to track the dispensed drug, as well as systems and corresponding methods thereof.

BACKGROUND

Various illnesses and disorders require multiple injections to control or treat a physiological condition. For example, insulin-dependent diabetics are required to inject several injections of insulin, of one or more types, each day, to control their blood sugar levels. In order to track the treatment, insulin-dependent diabetics are required to log each injection, as well as their blood sugar levels, in a log book at the time of injection. The data records can be used by the user to follow up on the therapy plan. A physician can retrospectively analyze the data to adjust the therapy if needed. Proper data recording is important to achieve improvement in treatment.

Patients, such as diabetics, during the course of their daily treatment, may use more than one injection device, disposable or reusable, to inject insulin, of the same or different type. Therefore it is desirable to have a simple, inexpensive device and method which is capable of capturing and recording all injection events from one or more injection devices.

SUMMARY

Tracking devices are used for tracking activities related to injection of a drug. The performance of the tracking device should be precise to prevent erroneous medical treatment. For example, failure of the tracking device in detecting an injected drug dose or false detection of an injection, may result in erroneous medical decisions.

Though the requirement for detection precision is high, there are many interferences, such as difficulty in accurately sensing the setting of a drug dose and/or injecting the drug dose, due to background disturbances or inadvertent movement of the injection device and irregular use of the injection device.

There is thus provided according to some embodiments, a tracking device comprising a comprehensive configuration, such as more than a single sensor. The signals emitted by the sensors may be processed by processes optimized for accuracy, such as by image classification processes.

According to some embodiments there is provided a drug tracking device used in combination with a drug injection device, the drug tracking device comprises a housing configured to engage with the drug injection device, an optical sensor configured to capture an image of a portion of the drug injection device, the portion of the drug injection device displaying indicia of drug doses, such that a captured image includes at least one indicia of a drug dose, a memory module having pre-stored indicia of drug doses, and a processor having instructions operating thereon configured to cause the processor to determine an injected drug dose by comparing at least one indicia of the drug dose in the captured image with the pre-stored indicia of drug doses.

In some embodiments, the pre-stored indicia of drug doses includes at least one of: pixels corresponding to the indicia of drug doses, and statistical values corresponding to the indicia of drug doses.

In some embodiments, the portion of the drug injection device displaying indicia of drug doses includes at least a portion of a display window displaying the at least one indicia of drug dose. In some embodiments, the drug tracking device further includes at least one sensor configured to detect injection of the drug. In some embodiments, upon detection of the injection of the drug by the at least one sensor, the optical sensor is activated to capture the image including the at least one indicia of the drug dose for use in determining the injected drug dose.

In some embodiments, the drug tracking device further includes at least one of: an additional optical sensor, a vibration sensor, an accelerometer, an auditory sensor, a temperature sensor, a movement sensor, and a magnetic sensor. In some embodiments, the optical sensor includes at least one of: a camera, a CCD, a CCD array, a CMOS sensor, a photodiode, a laser diode, a waveguide, and a lens.

In some embodiments, at least one of the drug tracking device and the drug injection device further includes a light source configured to illuminate at least the portion of the drug injection device displaying the indicia of drug doses.

In some embodiments, the drug tracking device further includes a signal filter configured to ensure the optical sensor captures a readable image for the processor to compare with the pre-stored indicia of drug doses. In some embodiments, the drug tracking device further includes at least one additional sensor, and wherein the processor further includes a signal processor configured to analyze signals from at least one of the optical sensor and the at least one additional sensor.

In some embodiments, wherein the processor includes a classifier including at least one of an image classification module and an image comparing module. In some embodiments, the processor includes at least one of a timer and a clock configured to calculate time information associated with an injection performed by the drug injection device. In some embodiments, the instructions are further configured to cause the processor to verify alignment of the drug tracking device with the drug injection device. In some embodiments, upon engagement of the drug tracking device and the drug injection device, the optical sensor captures at least one image of the portion of the drug injection device.

In some embodiments, the plurality of pre-stored images are saved by the memory module and may be used as the pre-stored indicia of drug doses. In some embodiments, the memory module further includes a pre-stored calibration image, and the instructions are further configured to cause the processor to verify alignment of the drug tracking device to the drug injection device by comparing the captured at least one image with the pre-stored calibration image. In some embodiments, the drug tracking device further includes a power source and/or an image processor. The image processor may be configured with instructions operating thereon to cause the image processor to perform at least one of edge detection, boundary detection, sharpness enhancing, object recognition, image segmentation, and video tracking on at least the captured image. The instructions operating on the processor may be further configured to identify a dose number appearing on the captured image using image classification.

In some embodiments, image classification includes comparing the captured image with the pre-stored indicia of drug doses. The pre-stored indicia of drug doses may include a collection of pre-stored images and corresponds to deliverable dose units contained in the drug injection device. In some embodiments, the image classification includes comparing at least one of pixel patterns and/or vectors of the captured image with each of the pre-stored images until the at least one of pixel patterns and/or vectors of the captured image match a corresponding one of the pre-stored images.

In some embodiments, the instructions operating on the processor are further configured to identify the injected drug dose via image classification, wherein image classification includes determining a statistical value corresponding to a number of black pixels corresponding to each of the indicia of drug doses in the pre-stored indicia of drug doses, determining a statistical value corresponding to a number of black pixels in the captured image, and comparing the statistical value corresponding to the pre-stored indicia of drug doses with the statistical value corresponding to the captured image to determine the injected drug dose.

In some embodiments, the determined statistical value corresponding to the pre-stored indicia of drug doses and the determined statistical value corresponding to the captured image each include at least one of: x-axis distributions of black (or white) pixels and y-axis distributions of black (or white) pixels. In some embodiments, the statistical value corresponding to the captured image is performed on a selected area of the captured image. In some embodiments, the determined statistical value corresponding to the pre-stored indicia of drug doses and the determined statistical value corresponding to the captured image each include a spatial distribution of areas of white (or black) pixels.

In some embodiments, the memory module is further configured to store the injected drug dose determined by the processor. In some embodiments, the instructions operating on the processor causes the processor to compare the at least one indicia of the drug dose in the captured image with the pre-stored indicia of a most recent stored injected drug dose and successive pre-stored indicia of drug doses.

In some embodiments, the drug tracking device further includes at least one of an auditory sensor and a vibration sensor, wherein the instructions are further configured to cause the processor to determine, based on signals received from the at least one of the auditory sensor and the vibration sensor, that the injected drug dose has been set. Once the dose has been set, to activate the optical sensor to capture the captured image, and determine the injected drug dose.

In some embodiments, the instructions are further configured to cause the processor to distinguish between signals from the at least one of the auditory sensor and the vibration sensor corresponding to setting the injected drug dose and to injecting the injected drug dose. In some embodiments, the instructions are further configured to cause the processor to distinguish, based on signals from at least one of: the auditory sensor, the vibration sensor, the optical sensor and a timer, whether, in respect to at least one of the following: the injected drug dose is set and injected, whether a small priming dose is set and injected into air, whether the injected drug dose is set and not injected, whether an inadvertent drug dose is set, whether the inadvertent drug dose is set and injected into air, whether the inadvertent drug dose is set and partially injected, whether the inadvertent drug dose is set at a partial unit, whether a click is generated during setting the drug or injecting the drug.

In some embodiments, the indicia of drug doses include a plurality of markings on the drug injection device. The markings may include any one of alphanumeric characters, a portion of the alphanumeric characters and a combination of alphanumeric characters and non-alphanumeric characters. The alphanumeric characters may include numbers and wherein the non-alphanumeric characters include at least one of dash lines and white spaces. In some embodiments, the numbers are even numbers and dash lines represent odd numbers.

According to some embodiments there is provided a drug tracking device used in combination with a drug injection device, the drug tracking device includes a housing configured to engage with the drug injection device, an optical sensor configured to capture an image of a portion of the drug injection device, the portion of the drug injection device displays indicia of drug doses, such that a captured image includes at least one indicia of a drug dose, a memory module has pre-stored indicia of drug doses, and a processor has instructions operating thereon to cause the processor to activate an image classification process operative to identify an injected drug dose by comparing the captured image with the pre-stored indicia of drug doses.

In some embodiments, the pre-stored indicia of drug doses stored in the memory module include a collection of images showing indicia of drug doses. In some embodiments, the indicia of drug doses include alphanumeric characters and non-alphanumeric characters. In some embodiments, the alphanumeric characters include numbers and the non-alphanumeric characters include at least one of dash lines and white space.

According to some embodiments there is provided a drug tracking device used in combination with a drug injection device having a rotation knob to set a drug dose, the drug tracking device includes a housing configured to engage with the drug injection device, an optical sensor configured to capture an image of a portion of the drug injection device, the portion of the drug injection device displays indicia of drug doses, such that a captured image includes at least one indicia of the set drug dose, a vibration sensor configured to detect rotations of the rotation knob to determine the set drug dose, and injection of the set drug dose, a memory module having pre-stored indicia of drug doses, and a processor having instructions operating thereon to identify the set drug dose by comparing the captured image with the pre-stored indicia of drug doses to determine the set drug dose, and detecting the injection of the set drug dose.

In some embodiments, the processor has instructions operating thereon to perform at least one of edge detection, boundary detection, sharpness enhancing, object recognition, image segmentation, and video tracking on the captured image. In some embodiments, the processor has instructions operating thereon to identify the indicia of the set drug dose appearing on the captured image using image classification. In some embodiments, the image classification includes comparing the captured image with the pre-stored indicia of drug doses, said pre-stored indicia of drug doses includes a collection of pre-stored images and corresponds to deliverable dose units contained in the drug injection device. In some embodiments, the image classification includes comparing at least one of pixel patterns and/or vectors of the captured image with each of the pre-stored images until the at least one of pixel patterns and/or vectors of the captured image match a corresponding one of the pre-stored images.

In some embodiments, the processor has instructions operating thereon to identify the injected drug dose via image classification, wherein image classification includes determining a statistical value corresponding to a number of black pixels corresponding to each of the indicia of drug doses in the pre-stored indicia of drug doses, determining a statistical value corresponding to a number of black pixels in the captured image, and comparing the statistical value corresponding to the pre-stored indicia of drug doses with the statistical value corresponding to the captured image to determine the injected drug dose.

In some embodiments, the determined statistical value corresponding to the pre-stored indicia of drug doses and the determined statistical value corresponding to the captured image include at least one of the x-axis distributions of black pixels and y-axis distributions of black pixels.

In some embodiments, the statistical value corresponding to the captured image is performed on a selected area of the captured image. In some embodiments, the determined statistical value corresponding to the pre-stored indicia of drug doses and the determined statistical value corresponding to the captured image each include a spatial distribution of areas of white pixels. In some embodiments, the processor further has instructions operating thereon to identify the set drug dose by counting rotations of the rotation knob detected by the vibration sensor. In some embodiments, the vibration sensor is further configured to distinguish between rotations of the rotation knob in a first direction and rotations of the rotation knob in a second direction.

In some embodiments, the processor further has instructions thereon to count rotations of the rotation knob in the first direction, count rotations of the rotation knob in the second direction, and subtract rotations in the second direction from rotations in the first direction to determine a counted drug dose. In some embodiments, the processor further has instructions thereon to verify that the counted drug dose matches the set drug dose.

According to some embodiments, there is provided a method for determining an injected drug dose from an injection device, the injection device including a window displaying a set drug dose and generating a series of click signals, the method including capturing, via an optical sensor configured to capture images through the window of the injection device, a plurality of images of a dose ring of the injection device for pre-storage of the images, detecting, via a sensor, at least one click signal generated by setting the set drug dose on the injection device, capturing, via the optical sensor, an image of dosage markings on the dose ring before the injection device injects a drug, detecting, via the sensor, at least one click signal generated by injecting the set drug dose, comparing, via a processor, the image to the plurality of pre-stored images to determine the injected drug dose.

In some embodiments, the injected drug dose is determined when features of the image match features of one of the plurality of pre-stored images. In some embodiments, the matched features include at least one of pixels, pixel patterns, pixel vectors, and statistical values. In some embodiments, the method may further include storing, at a memory, the matched one of the plurality of pre-stored images, detecting, via the sensor, at least a second click signal generated by setting a second set drug dose on the injection device, capturing, via the optical sensor, a second image of dosage markings on the dose ring before the injection device injects a second amount of drug, detecting, via the sensor, at least one second click signal generated by injecting the second set drug dose, comparing, via the processor, the second image to subsequent images from the plurality of pre-stored images, the subsequent images from the plurality of pre-stored images having higher doses compared to the matched one of the plurality of pre-stored images, and determining, via the processor, the second injected drug dose when features of the second image match features of one of the subsequent images from the plurality of pre-stored images.

According to some embodiments there is provided a method for detecting injection of a drug from an injection device, the injection device includes a window displaying a drug dose and generating a series of click signals, the method includes capturing, via an optical sensor, a first image of the window before the injection device injects a drug, processing, via a processor, the first image to identify a first drug dose displayed on the window, detecting, via a sensor, a vibration signal having a vibration amplitude generated during injection, capturing, via the optical sensor, a second image of the window after the injection device injects the drug, processing, via the processor, the second image to identify the second drug dose displayed on the window, calculating, via the processor, an average click signal by dividing the vibration amplitude by the difference between the first drug dose and the second drug dose, and comparing, via the processor, an average click signal with a predetermined click threshold to detect injection.

BRIEF DESCRIPTION OF THE DRAWINGS

FIGS. 1A-1C are each a schematic illustration of an exemplary drug dispensing-tracking system in an assembled state (1A), in a disassembled state (1B) and an exploded view of a tracking device (1C) of the drug dispensing-tracking system, constructed and operative according to some embodiments of the present disclosure;

FIGS. 2A and 2B are each a block diagram of components of a drug dispensing-tracking system (2A) and of a processor of a drug dispensing-tracking system (2B), constructed and operative according to some embodiments of the present disclosure;

FIGS. 5A and 5B are each a graphic representation of a predetermined value used in the image classification process of respective FIGS. 4A and 4B;

FIGS. 11A and 11B are a schematic illustration of an exemplary drug dispensing-tracking system at two operational stages constructed and operative according to some embodiments of the present disclosure.

Figure 1A:
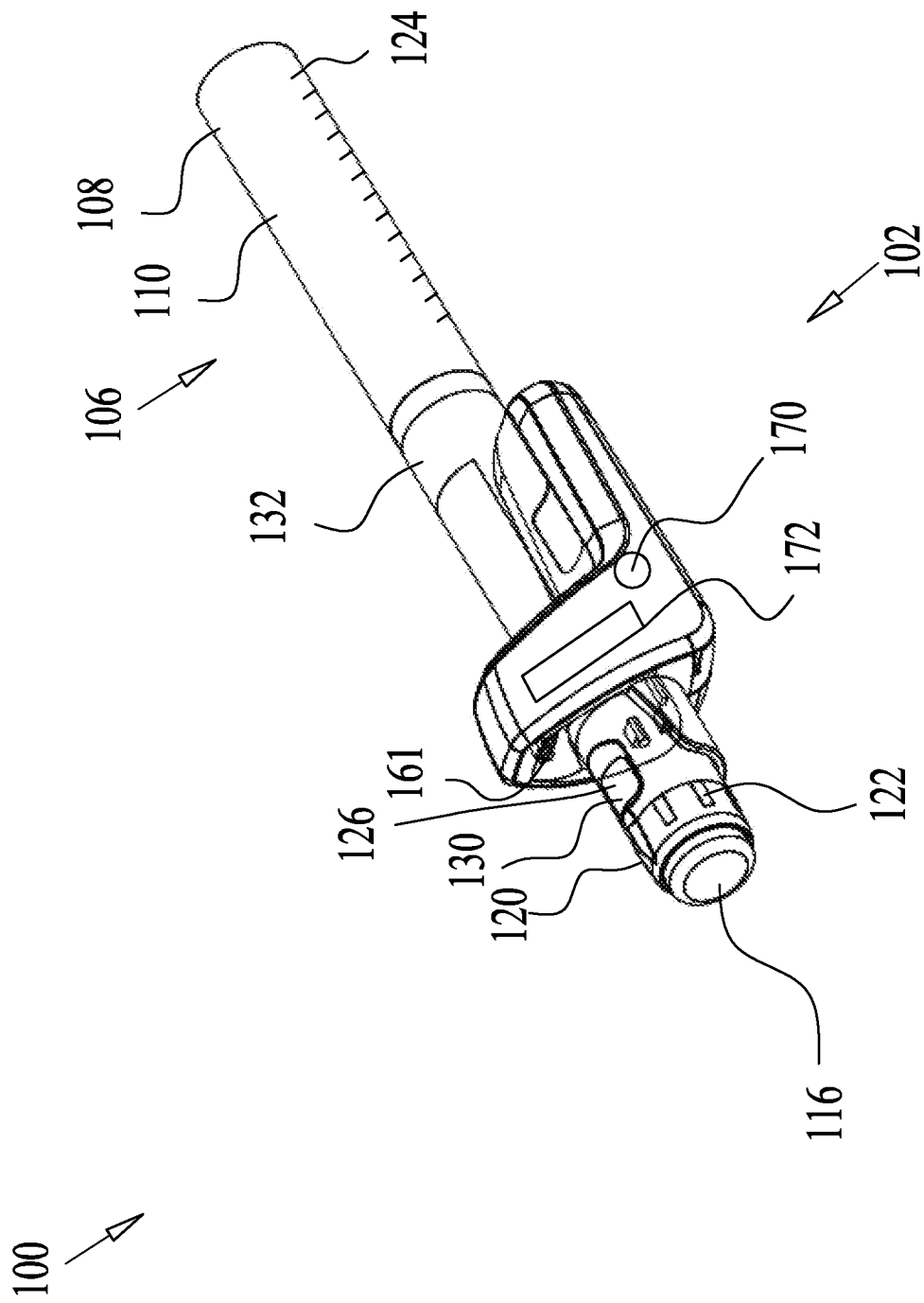

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The principles and operations of the systems, apparatuses and methods according to some embodiments of the present disclosure may be better understood with reference to the drawings, and the following description. The drawings are given for illustrative purposes only and are not meant to be limiting.

DETAILED DESCRIPTION

Figure 1B:
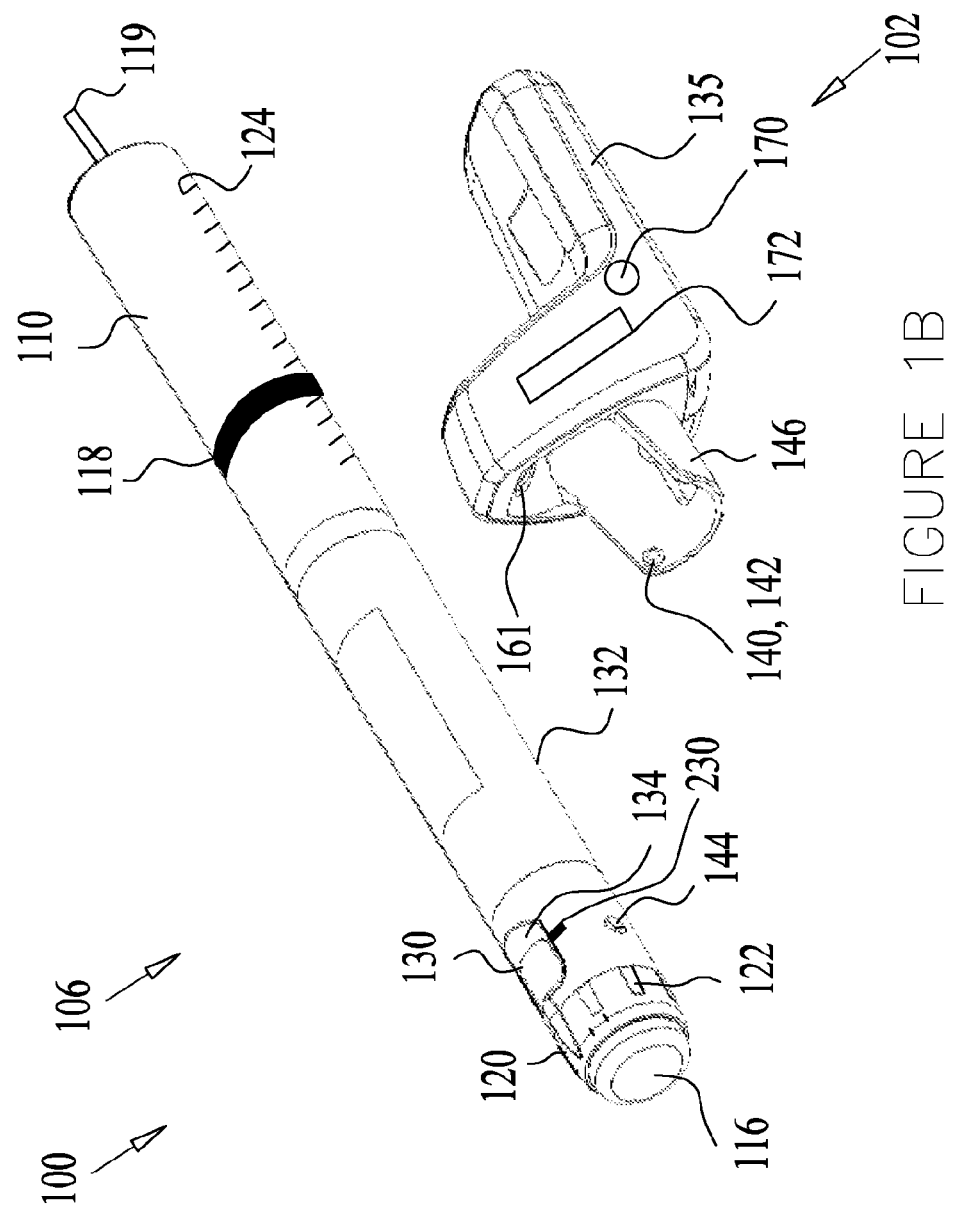

FIGS. 1A-1C are illustrations of an exemplary drug dispensing-tracking system 100 according to some embodiments of the present disclosure. The drug dispensing-tracking system 100 may comprise a tracking device 102 used in combination with a drug-injection or drug storage device 106.

As seen in FIGS. 1A and 1B, the injection device 106, configured for injection of a drug into a user, such as a patient, may comprise a shaft 108. The shaft 108 may comprise a first portion including a drug reservoir 110 containing a drug, which may be at least partially transparent or may be covered. Following selection of a desired drug dose, the drug may be injected by pressing an injection button 116 (e.g. a push-button) which urges the advancement of a piston 118 (FIG. 1B) for dispensing the drug from the drug reservoir 110 through a needle 119 into a patient/user.

In some embodiments, a desired dose of injected drug may be determined by rotating a rotation knob 120. The rotation knob 120 may comprise a plurality of notches 122 or any other indicator. The rotation of the knob 120 to a first direction (e.g. clockwise) is performed to set the delivered drug dose. In some injection devices 106 the rotation of the knob 120 to a second, opposite direction (e.g. counterclockwise) is performed to correct (e.g. decrease), if necessary, the drug dose. In some embodiments, the rotation of the knob 120 to the first or second direction may be accompanied by a clicking sound. These sounds may be distinguishable when properly analyzed, as will be described.

The predetermined dose of the drug released by the rotation of a notch 122 may be different in various injection devices 106. In a non-limiting example, the released dose may be of a single unit, 2 units or 3 units, or a half of a unit. When the drug is insulin, a single drug unit may comprise 0.01 milliliters, for example. Thus, the rotation of a single notch 122 may correspond to a single unit of 0.01 milliliters of insulin, two units (0.02 ml), three units (0.03 ml), or a half of a unit (0.005 ml).

The type of drug may be different in different injection devices 106. In a non-limiting example, during the treatment course of a diabetic patient, different types and/or quantities of insulin are administered, such as a basal insulin dose and a bolus insulin dose. The different doses may be injected by different injection devices 106. Accordingly, a patient may routinely use more than one drug-injection device 106 during the course of his daily treatment.

Figure 9:
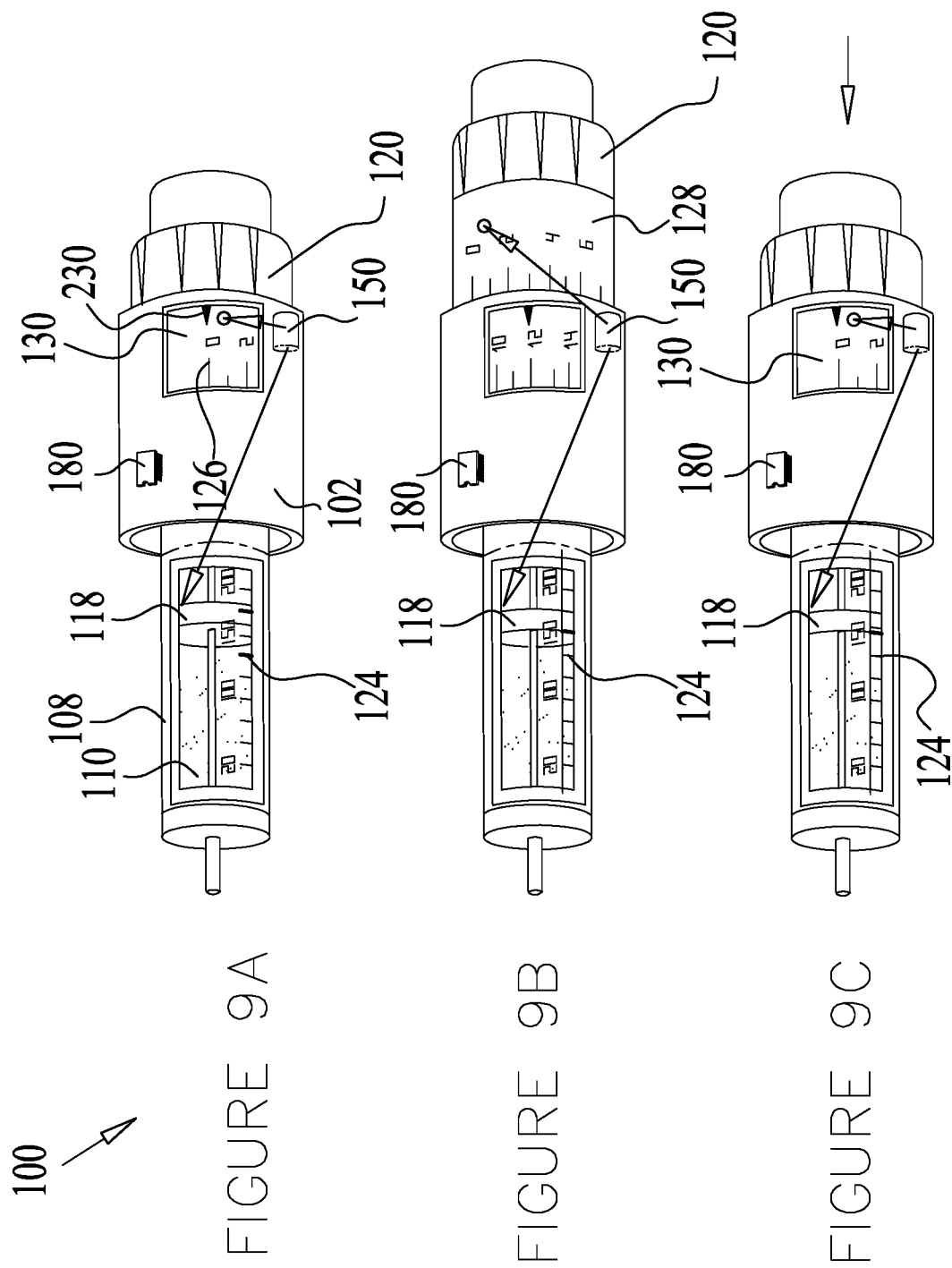
FIGS. 9A-9C are a schematic illustration of an exemplary drug dispensing-tracking system at three operational stages constructed and operative according to some embodiments of the present disclosure.

In some embodiments, reservoir scale and/or numerical markings 124 may be formed on the reservoir portion 110 and are indicative of the volume of drug contained in the injection device 106. Alternatively or additionally, scale and/or numerical dose markings 126 may be formed on the circumference of an inner cylinder 128 (FIG. 9B and also referred to as a "dose ring") of the shaft 108. Dose markings 126 are indicative of the drug dose selected by rotation of the knob 120. Images of dose marking 126 are shown in FIGS. 4A-4D. Rotation of the knob 120 causes rotation of inner cylinder 128, formed thereon with the dose markings 126. The dosage marking 126 is displayed at a display window 130. An outer cylinder 132 overlies the inner cylinder 128 and is formed with an aperture 134 (FIG. 1B) exposing the display window 130.

In some embodiments, the injection device 106 may comprise an injection pen. The injection pen may be disposable, configured for limited or even single use or may be configured for multiple uses and fitted to receive replacement cartridges or vials. In some embodiments, the injection device 106 may comprise a syringe, such as a reusable or disposable syringe. In some embodiments the injection device 106 may include any drug storage device.

The tracking device 102 may be engaged with the injection device 106 in any suitable manner, such as being formed as an insertable unit, as shown in FIGS. 1A-1C. In some embodiments, the tracking device 102 may be formed as a cap designed to be inserted on the injection device 106. In some embodiments, the tracking device 102 may be integrated with the injection device 106, together formulating a monolith device. In some embodiments, the tracking device 102 may be configured to operate remotely from the injection device 106 and may communicate wirelessly therewith.

The tracking device 102, shown in FIGS. 1A-1C, may be coupled to the injection device 106 in any suitable manner. The tracking device 102 may comprise a housing 135 which may be formed of a base 136 and a cover 138. The housing 135 is formed to be inserted on the drug injection device 106. In some embodiments, the housing 135 may be formed with attachment means 140 which may comprise structural features for fitting onto the injection device 106. For example, the housing 135 may be formed with protrusions 142 for mating with corresponding manufactured recesses 144 on the injection device 106.

In some embodiments, the attachment means 140 may comprise any structure for attaching the tracking device 102 to the injection device 106, such as clips, clasps, adhesives, and the like.

In a non-limiting example, the injection device 106 may comprise a commercially available pen and the structural features may be constructed according to the corresponding structural features of a selected injection device 106. Alternatively, the structural features of the tracking device 102 may be formed to fit a plurality of types of injection devices 106.

In some embodiments, the housing 135 may be further formed with flanges 146 or any other suitable structure for securely aligning the tracking device 102 with the injection device 106.

As seen in FIG. 1A, the cover 138 may be formed at an incline or in any suitable manner to be in proximity to the window 130 while the window 130 is exposed to the user's view. In some embodiments, the tracking device 102 may be formed with an aperture aligned with the window 130. In some embodiments, the housing 135 may comprise a transparent element or portion covering the area of the window 130 for allowing a direct, unobstructed view of the window 130 from the optical sensor 152 (FIG. 2A), such as a camera 161 shown in FIGS. 1A-1C.

The tracking device 102 is configured for detecting activities related to the delivery of a drug. These activities may comprise detecting, inter alia, the injected dose of a drug; the volume of drug remaining in the injection device 106 following the drug injection; the time of injection; the time duration since the previous injection; the age of the drug, such as the time passed since the manufacturing of drug; the time passed since initial use of drug; the expiration date of the drug; the bioavailability of the drug; the optical quality of the drug; the degree of cloudiness of the drug; the temperature of drug; the type of drug; the type of injection device 106, as well as additional drug related data.

Figure 2B:
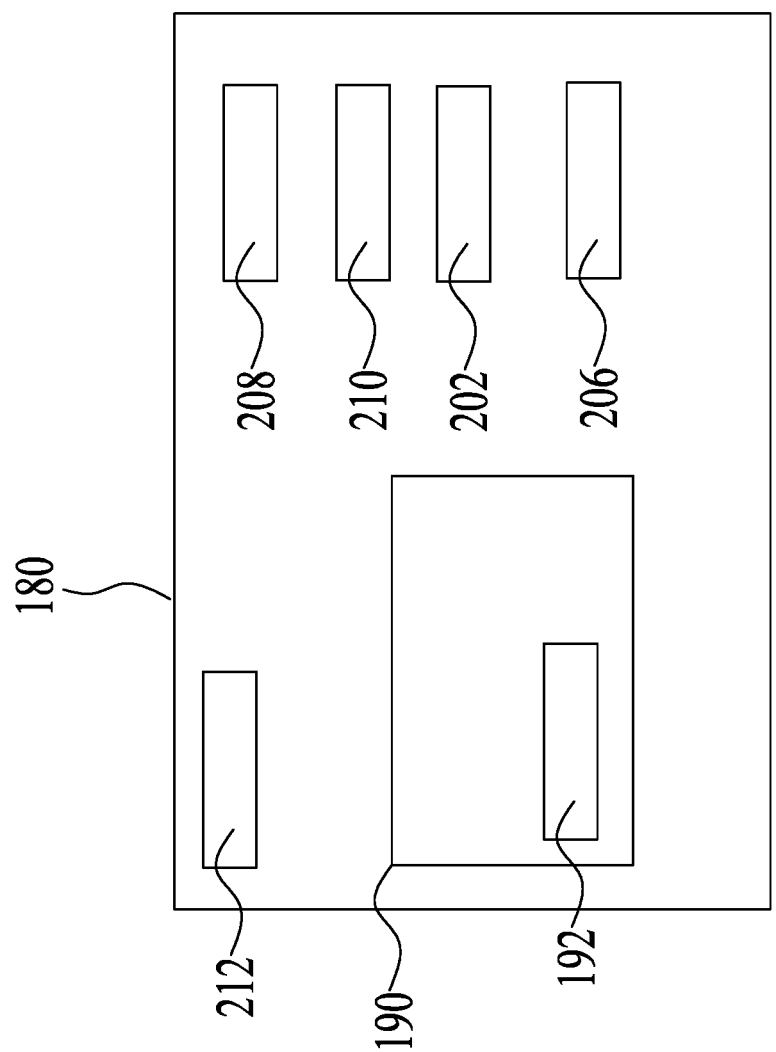

FIGS. 2A and 2B illustrate components of the drug dispensing-tracking system 100 (FIG. 2A) and of a processor (FIG. 2B) in a block diagram. The tracking device 102 may comprise at least one sensor 150 for detecting the activities related to the delivery of a drug, such as detecting the injected drug dose. For example, the sensors 150 may comprise a dose setting sensor for detecting the set drug dose and/or the injected drug dose. In another example, the sensors 150 may comprise an injection sensor for detecting the event of injecting the drug into the user.

Figure 10:
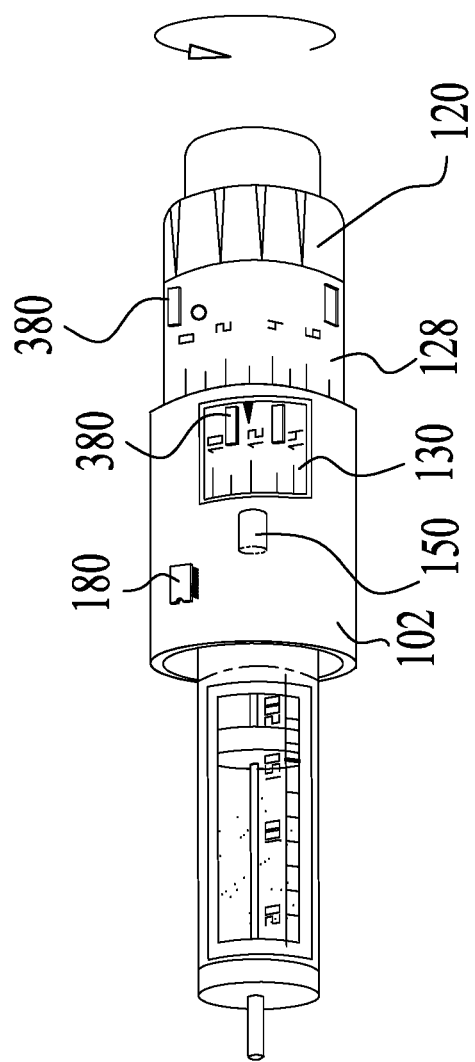
FIG. 10 is a schematic illustration of an exemplary drug dispensing-tracking system constructed and operative according to some embodiments of the present disclosure.

In some embodiments, a plurality of sensors 150 may be provided, such as at least one or more of an optical sensor 152 and a vibration sensor 154. In some embodiments, further sensors may be provided such as an auditory sensor 156, a temperature sensor 158, movement sensors and/or magnetic sensors (e.g. as shown in FIG. 10).

In some embodiments, an illuminator or light source 160 may be paired with the optical sensor 152 so as to light up the display window 130.

The optical sensor 152 may comprise a camera 161 (FIGS. 1A-1C), a CCD, a CCD array, a CMOS sensor, a photodiode, a laser diode, a waveguide, a lens or any other means for imaging. In some embodiments, the optical sensor 152 may be paired with the light source 160, such as an array of LEDs or other optical devices, such as lenses, beam splitters, and further optical devices for detecting a drug related activity.

In some embodiments, the optical sensor 152 may be positioned at an incline for capturing an image of the display window 130 and may be supported by an internal flange 162 (FIG. 1C). In some embodiments, additional optical sensors 152 may be provided to image other sections of the drug injection device 106, such as the marking 124 or piston 118.

In some embodiments, a signal filter 164 may be provided to filter any one of the signals received from the sensors 150. For example, the signal filter 164 may comprise an optical filter, such as a lens, a diffuser or an Infra-Red emitter operative to generate light at a selected wavelength to prevent glaring caused by ambient light, surrounding the tracking device 102. The optical filter may be configured to prevent optical aberrance and allow the optical sensor 152 to effectively capture an image. In some embodiments, signal filter 164 may be configured to ensure the optical sensor 152 captures a readable image allowing the processor 180 to compare the captured image with a prestored indicia of the drug dose.

In some embodiments, the optical sensor 152 may be paired with the light source 160, to operate in synchronization therewith such that images will be captured in conditions that allow for filtering unwanted stray or ambient light. For example, images captured when the light source 160 is on could be subtracted from images captured when the light source 160 is off. The difference in the light level may be the ambient light level and thus may be filtered from a captured image.

Additionally, use of the light source 160 can enable image capturing (and thus dose tracking) at poor light conditions.

The vibration sensor 154 may comprise an accelerometer 166 (FIG. 1C) comprising, for example, piezoelectric, piezoresistive and/or capacitive components and/or may include a MEMS (micro electro-mechanical system) device, for example.

The auditory sensor 156 may comprise a microphone 167 of any suitable configuration, such as an analog device including a low noise microphone, such as the ADMP504 or ADMP521 component or a device including an ADMP441-I2S component.

Any one of the sensors 150 may be provided in a form of an array of sensors arranged in any suitable manner, such as an array of CCDs or an array of accelerometers, for example.

In some embodiments, any one of sensors 150 may be arranged as separate components, auxiliary to the housing 135 of the tracking device 102 and in communication with the tracking device 102 and/or the injection device 106 and/or an external device 176.

An indicator 168 may be provided to indicate the state of the tracking device 102 and/or drug injection device 106 and may provide alerts, as well. The indicator 168 may comprise a light signal, such as a LED (170 in FIGS. 1A-1C), and/or an indication panel 172.

The LED 170 may be configured to display alerts and messages to the user, such as by colors used at different intervals (e. g. flashing or steady). For example, a green light may illuminate upon proper alignment of the tracking device 102 with the injection device 106, as will be described at step 300 in FIG. 3A.

The panel 172 may be configured as a user interface to display alerts and messages to the user and to receive input from the user.

In some embodiments, the indicator 168 may be a display module, such as a screen of an external unit 176. The external unit 176 may run an Application thereon configured to communicate alerts and messages to the user and to receive input from the user. In some embodiments, the indicator 168 may comprise an acoustical signal, such as a buzz or other sound, to alert the user.

The following are some but not all examples of various states and alerts: a degree of alignment of the tracking device 102 with the drug injection device 106; the battery charging level; Bluetooth or any other communication connection; alert that the cover of the drug-injection device 106 was not returned after use; alert set prior to a meal to remind to partake a meal and/or an injection; alert generated after a passage of a predetermined time span reminding the user that another injection is due; alert to inform the user of a missed injection; alert in case of an error caused by multiple injections; alert if a higher or lower than average dose is detected or of any deviation from past historical injections;

alert pertaining to the drug such as overheating or cooling of the drug, (the temperature of the drug may be measured by the temperature sensor 158); alert pertaining to the drug bioavailability (i.e. the loss of the drug efficacy over time due to heating, this may be measured via the temperature sensor 158 over a predetermined time span); alert on passage of a predetermined time period (e.g. 30 days) from commencement of use of the injection device 106; and alert if the volume of the drug remaining in the injection device 106 is lower than a predetermined threshold.

In some embodiment, the tracking device 102 may comprise a communication module 178 for transmitting signals and alerts to the external unit 176 and/or the injection device 106, and for receiving signals indicative of data therefrom. The communication module 178 may be configured for wired or wireless communication, via an analog short range communication mode, or a digital communication mode including WIFI or Bluetooth and/or via a network, for example.

The sensor 150 may transmit a signal to a processor 180, which may be embodied in a printed circuit board (PCB) assembly 184 (FIG. 1C) inserted within the base 136. A power source 186, such as a battery, may be positioned within the base 136 or at any other location.

The optical sensor 152 and indicator 168 may be connected to the PCB assembly 184 in any suitable manner such as via a flex cable, for example.

A processor 180 is provided to control the operation of the tracking device 102 and its components.

Some features of the processor 180 are schematically shown in FIG. 2B and may represent physical or functional components or modules embodied in the processor 180. It is noted that any one of these features may be embedded within the processor 180 or may be a feature external thereto, such as a feature embedded in the external device 176.

The processor 180 may comprise a signal processor 190 for processing signals provided thereto, such as from the sensors 150. The signal processor 190 may further function as an analyzer configured for analyzing the signals. The signal processor 190 may include an image processor 192 configured to process images provided by the optical sensor 152. The image processor 192 may function as an analyzer configured to analyze the image, image data, and indicia of a drug dose, a drug injection or any other drug related information. Further analysis and processing functions may be deployed by a classifier 202, which is an image classification module, or image comparing module, operative to compare images, such as for deploying an image classification process (ICP). In some embodiments, the classifier 202 may be operative to compare an image captured by the optical sensor 152, with a prestored (i.e pre-stored) image, stored within a memory module 206. The memory module 206 may be further configured for short and/or long term storage of additional signals and data. The image may comprise indicia of drug doses, such as markings on the drug injection device 106 at the window display 130, along the reservoir 110 or any other location. The indicia may comprise at least one of: alphanumeric characters, portions of the alphanumeric characters, non-alphanumeric characters, lines, arrows, pointers, spaces, white spaces.

A counter 208 may be provided, such as to count the vibration and acoustical signal(s) produces by rotation of the knob 120 or during injection (e.g. the "clicks"). The processor 180 may comprise a timer/clock 210 configured to calculate or indicate any time related information. For example, any activity detected by the tracking device 102 may be provided with a timestamp by the timer 210.

The processor 180 may comprise a controller 212 for managing the abovementioned features and executing instructions pertaining to the activity of the tracking device 102.

Figure 3A:
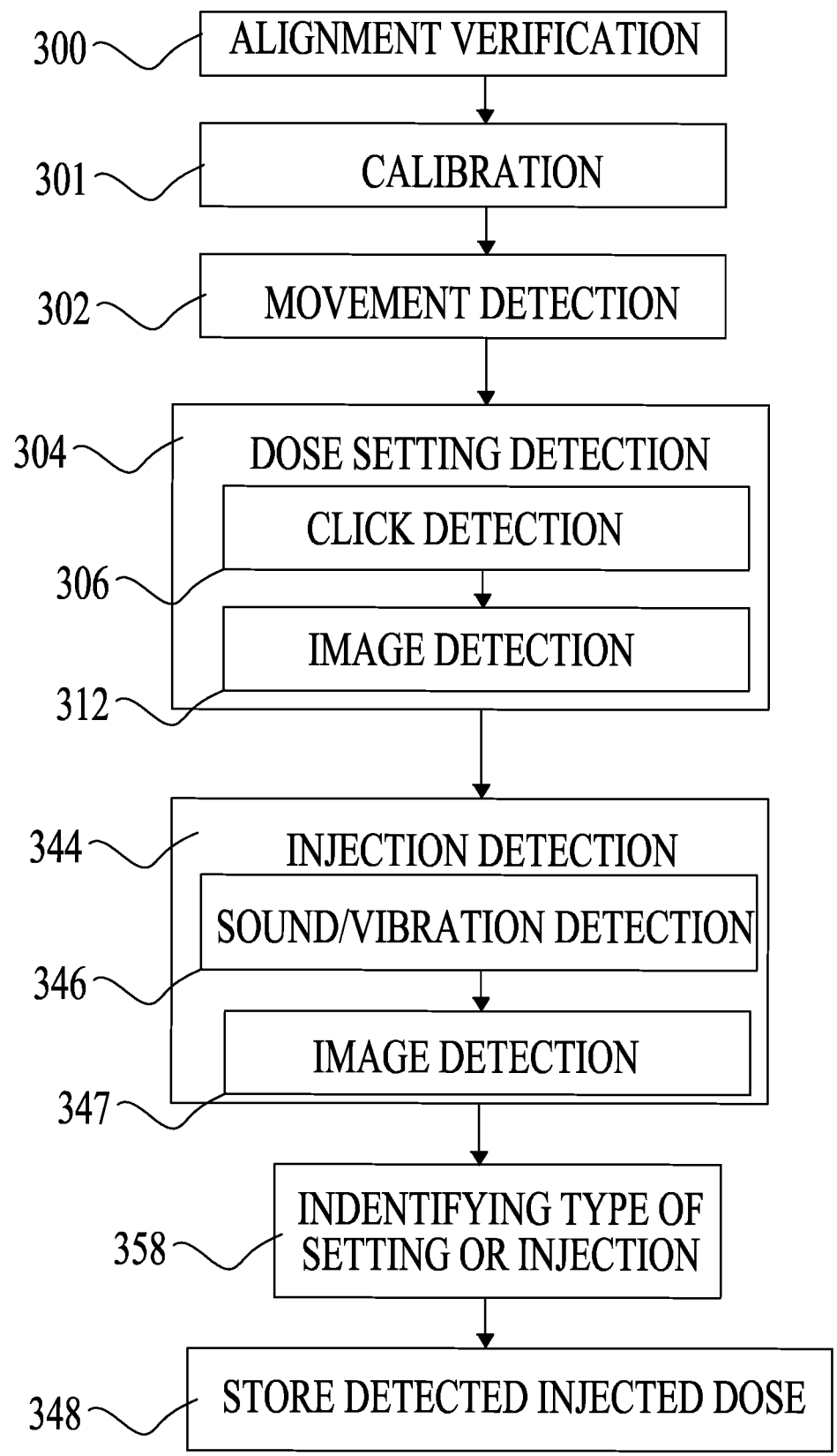
FIGS. 3A-3D are each an exemplary flow chart of a method for tracking an injected drug, constructed and operative according to some embodiments of the present disclosure.

FIG. 3A is an exemplary flowchart of a method for drug dose tracking. In some embodiments, at step 300, upon attaching the tracking device 102 with the injection device 106, the processor 180 may optionally verify the alignment of the tracking device 102 with the injection device 106, such as verifying that the optical sensor 152 can image the display window 130. If the alignment is not verified, an alert may be generated to the user via the indicator 168.

In some embodiments, the alignment verification may be performed by initially prestoring in the memory module 206 a prestored calibration image. The prestored calibration image may contain the window 130 with the tracking device 102 shown properly aligned therewith. For example, the prestored image may include a display of zero "0" in the window 130. In some embodiments, the prestored calibration image may comprise a plurality of prestored calibration images.

Prior to use of the tracking device 102, the processor 180 may be configured to capture the image of the window 130 and its surroundings and compare it with the prestored calibration image. Should a misalignment be detected, the processor 180 may be configured measure the coordinates of the misalignment by comparing the captured image with the calibration image by the classifier 202. The processor 180 may also be configured to alert the user (via indicator 168 and/or an Application running on an external device 176 (FIG. 2A)) as to the degree (i.e. the coordinates) of misalignment and/or guide the user to correctly position the tracking device 102 on the injection device 106.

In some embodiments, alignment verification step 300 may include requesting the user to rotate the knob 120 to zero which will prompt the optical sensor 152 to image the window and compare it with the prestored calibration image.

In some embodiments, the alignment verification step 300 may be performed until alignment is achieved.

In some embodiments, the alignment verification step 300 may be additionally performed at predetermined events or times during use of the injection device 106 along with the tracking device 102, such as prior to a new occurrence of an injection. This is performed to recalibrate the alignment of the injection device 106 with the tracking device 102, which may have been displaced during use.

In some embodiments, at step 301, calibration of the tracking device 102 may be further performed. The calibration step 301 may include the abovementioned request to the user to rotate the knob 120 to zero (step 300); the calibration step may further include rotation of the knob 120 to a predetermined dose to prerecord the click signals at different states such as: during rotation in a first direction and/or in a second direction, or during injection; the calibration step may further include requesting the user to input (e.g. in the Application or the panel 172) the current drug volume contained in the injection device 106. In some embodiments, the current volume contained in the injection device 106 may be determined by sensing a drug volume, weight, and/or location of the piston 118, such as by sensing the location of the piston 118 relative to markings 124.

To conserve energy, the tracking device 102 may assume a standby or low energy mode prior to activation of its components. At step 302, upon detection of some activity of the tracking device 102 or injection device 106, such as detection of movement of the tracking device 102 or injection device 106 by the vibration sensor 154, the sensors 150 may be prompted to initiate activity to detect an injected drug dose, as will be described in the following steps.

In some embodiments, the processor 180 may be configured to distinguish between slight, inadvertent movement of the injection device 106 and intentional grasping of the injection device 106 for injection thereof. This may be performed by calculating if a detected vibration sensed by the accelerometer 166, is above (or below) a predetermined threshold. Should the detected vibration be above (or below) the predetermined threshold, the sensors 150 may be prompted to activate the detection of an injected drug dose. The predetermined threshold may be prerecorded and indicative of grasping an object (e.g. the injection device 102).

In some embodiments, the dose setting may be detected at step 304, in any suitable manner and sequence. For example, as shown at step 306, the clicks, or any other sound or movement, generated by rotation of the knob 120 while setting the dose, may be detected by the vibration sensor 154 and/or the auditory sensor 156 and may be enumerated by the counter 208.

In an event the knob 120 is set by rotation in the first direction and thereafter correcting the setting by rotation in the second, opposite direction (to decrease the dose), the processor 180 may be configured to detect the directionality of the rotation, and subtract the enumerated clicks in the second direction from the enumerated clicks in the first direction.

In some embodiments, the detected vibration and/or auditory signal may be processed by the signal processor 190. In a non-limiting example, the signal processor 190, may be configured to calculate an average setting click, by measuring the total amplitude of the vibration or auditory signal generated during setting (e.g. as detected by decibels for an auditory signal, or as detected in Standard Gravity units, g, for a vibration signal). The total amplitude is divided by the number of clicks detected at step 306. This calculated average setting click may be compared with a predetermined setting amplitude threshold.

The predetermined setting amplitude threshold may be determined by: an amplitude provided by the injection device manufacturer; by prerecording a setting click following manufacture of the injection device and prior to use (typically under ideal, noiseless conditions); by requesting the user during the calibration step 301 to perform a calibration setting; and/or by any other method. The setting clicks may be recorded at different setting states, such as during rotation in the first direction, and/or rotation in the second direction and the like.

The average setting click may be compared to the predetermined setting amplitude threshold to identify and classify the type of setting (e.g. in the first direction and/or in the second direction).

Furthermore, by calculating the average click, a detected click deviating from the average click may be filtered, since it may be generated by inadvertent collision of the injection device 106.

The enumerated clicks may be stored in the memory module 206.

Following the auditory or vibration detection of the dose setting at step 306, the processor 180 may be configured to activate the optical sensor 152 for capturing the image of the selected dose displayed in the window 130, as shown at step 312. In some embodiments, the processor 180 may be configured to activate (i.e. "awaken") an otherwise dormant the optical sensor 152 in response to the vibration or auditory signals, thereby conserving energy of the power source 186.

In some embodiments, the captured image may be processed by the image processor 192, such as performing the process of edge detection and/or boundary detection for detecting the edges and/or boundaries of the captured image, and/or enhancing the sharpness of the black pixels of the captured image.

The captured image may be analyzed by the image processor 192 and/or classifier 202 for identifying the dose number appearing on the captured image. In some embodiments, the image identification may be performed by the classifier 202 configured to execute an Image Classification Process (ICP).

In some embodiments, the image classification process may comprise comparing the captured image with a collection of prestored images. The collection of prestored images may correspond to the volume of (or a number of) deliverable dose units contained in the injection device 106. Accordingly, the prestored images may include at least some or all potential images displayed in the window 130, running from "0" to the maximum number of drug units. For example, in an injection device 106 containing 80 units of the drug, the window will show a number running from 0 to 80 and thus the collection of prestored images may include 81 precaptured images.

In this example, the prestored images are stored in the memory module 206 prior to use of the tracking device 102 with the injection device 106. As such, the prestored images may be preprogrammed into the tracking device 102.

According to some embodiments, the image classification process may be deployed by comparing the pixel patterns and/or vectors of the captured image with each of the prestored images (i.e. pixel-to-pixel comparison). The classifier 202 may be configured to sequentially and/or recursively compare the captured image with the prestored images, until the captured image is matched with the correct corresponding prestored image. In a non-limiting example, in an event the set dose is of "8" drug units, the number displayed in the window 130 is "8". The captured image will comprise an image of "8". The classifier 202 may recursively compare the pixel pattern and/or vectors of the captured image with the prestored images, commencing at the image containing "0" until the prestored image containing the "8" is matched with the captured image. This pixel-to-pixel comparison of the captured image with the prestored image may be referred to as a correlation process.

Figure 3B:
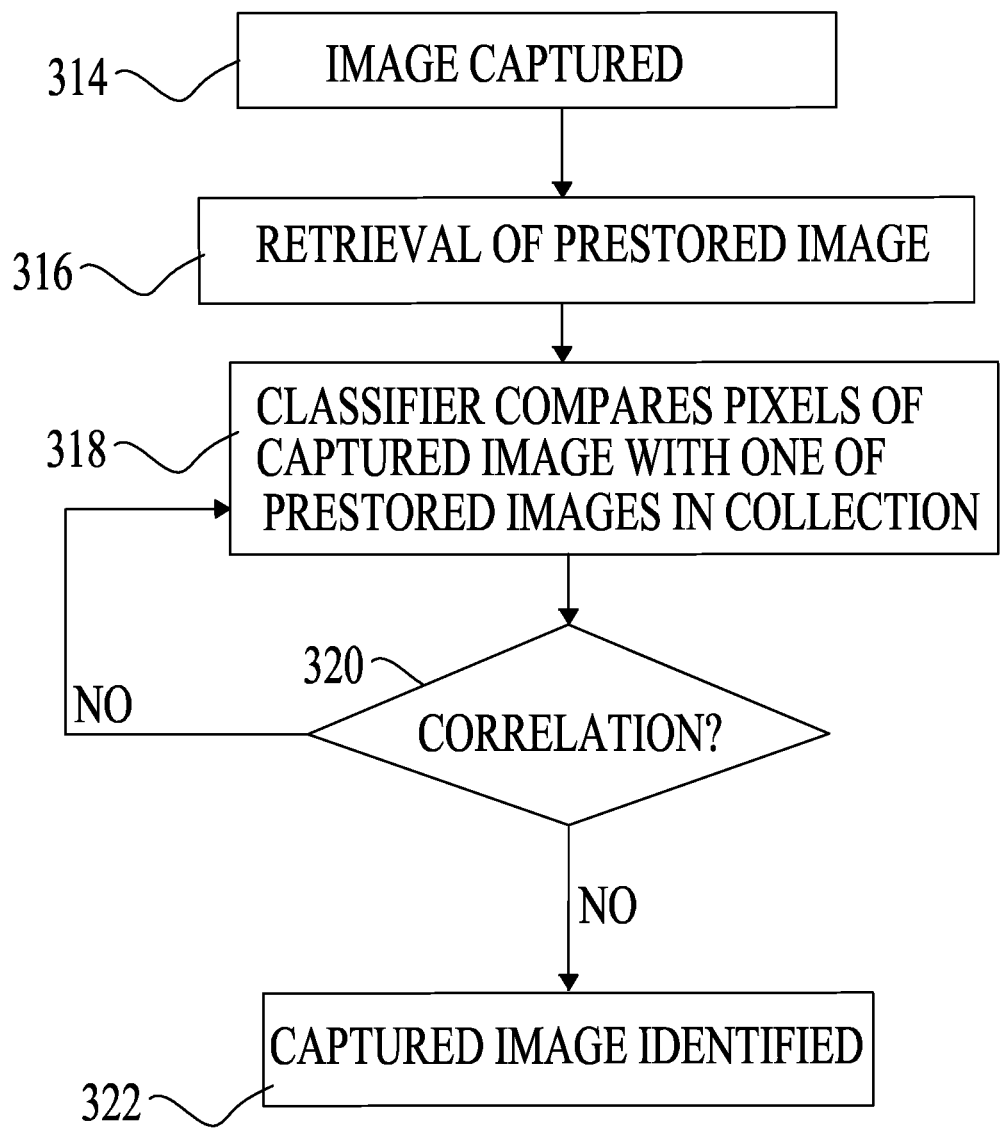

FIG. 3B is a flowchart of a non-limiting example of the correlation process. As seen at step 314 the image is captured by the optical sensor 152. At step 316 the collection of the prestored images are retrieved from the memory module 206. The correlation process commences at step 318 as the classifier 202 compares the pixel patterns and/or vectors of the captured image with the first prestored image. If the captured image correlates with the prestored image at step 320, the captured image is identified, as seen as step 322. If the captured image does not correlate with the prestored image, the correlation process continues with a subsequent prestored image, as shown at step 318, until the correlation is found. In some embodiments, if the captured image does not correlate with the prestored image, first step 316 may be performed for retrieving a subsequent prestored image and then the correlation process 318 is initiated again.

It is noted that the correlation of the pixels (or values of FIG. 3C) may be defined as a 100% match or in some embodiments by a substantial match, such as for example a 90% match, an 80% match, a 70% match, a 60% match, a 50% match, more or less, subranges and variants thereof.

In some instances, recursive correlation of the captured image with the series of the prestored images may be lengthily and energy consuming. According to some embodiments, the image classification process may be deployed by designating the prestored and captured image with a predetermined value. The classifier 202 may be configured to compare, and accordingly match, a designated predetermined value of the captured image with the designated predetermined value of the prestored image. Classifying the captured and prestored images, at least partially, based on the predetermined value, may be more efficient and rapid than pixel-to pixel-correlation.

In a non-limiting example, the predetermined value may be a statistical value or feature. This may be the number of black pixels in the image and the black pixel distribution on the image, namely the density distribution of the black pixels on the image. For example, as seen in schematic, simplified FIG. 4A, the image showing the number "8", contains 20 black pixels (each pixel represented by a box), which are positioned at the center of the image along the y-axis, and may be aligned with a dose arrow 230 of the injection device 106. For further clarification, the black pixel distribution value along the image y-axis is illustrated in the graph of FIG. 5A.

In FIGS. 5A and 5B, the vertical axis represents the number of black pixels and the horizontal axis represents the black pixel distribution on the image.

Figure 4B:
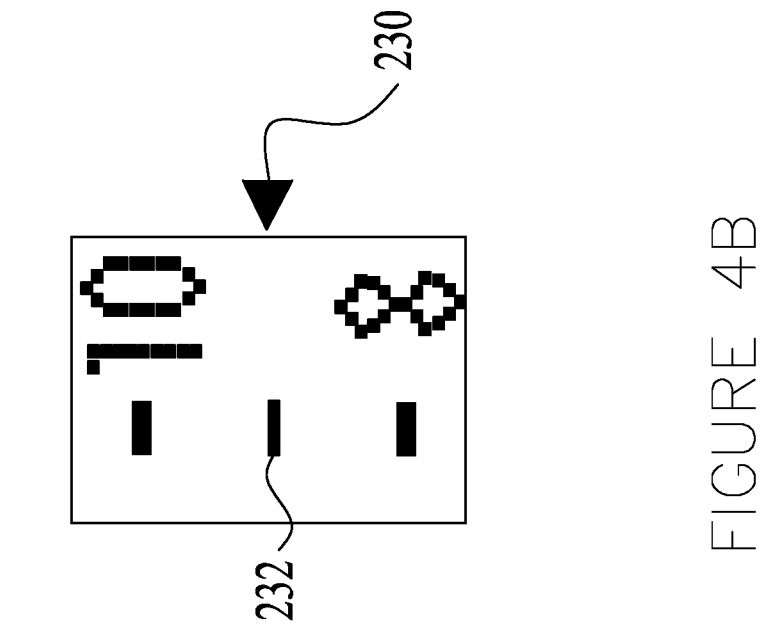
FIGS. 4A-4F are each a schematic illustration of an image processed by an image classification process deployed by the drug dispensing-tracking system, constructed and operative according to some embodiments of the present disclosure.

The image of FIG. 4B, shows the number "8" and "10" In this non-limiting example, the "8" numeral contains 20 black pixels and the "10" numeral contains 28 black pixels (i.e. 10 black pixels representing the "1" numeral and 18 black pixels representing the "0" numeral). The numerals "8" and "10" are each positioned at the periphery of the image. For further clarification, the black pixel distributions value is illustrated in the graph of FIG. 5B.

In general terms, a captured image may be analyzed by image processor 192 and/or classifier 202 to determine its predetermined value, and accordingly match it with a corresponding value of a prestored image. Thus by designating images with a predetermined value, the identification of the dose number appearing on the captured image may eliminate or minimize the pixel to pixel correlation with the prestored images, thereby optimizing the image identification procedure.

In another non-limiting example, the abovementioned predetermined value comprising the black pixel density distribution may be analyzed by the image processor 192 and/or classifier 202 to determine the parity of the imaged dose, namely, if the imaged dose is represented by an odd or even number. For example, this may be performed in injection devices 106 wherein even numbers are represented by numerals and odd numbers are represented by an intermediate tick mark only (also referred to herein as a dash line), as a shown in FIG. 4B, wherein the number "9" is represented by the tick mark/dash line 232 intermediate the even numbers "8" and "10."

In another non-limiting example, the abovementioned predetermined value comprising the black pixel density distribution may be analyzed by the image processor 192 to determine the numerical order of the imaged dose, namely if the imaged dose is represented by a single digit (i.e. a number between 0 and 9) or a double digit.

Thus it is demonstrated that to further optimize the image identification procedure, the image classification process may be configured to identify a group of numbers (e.g. odd or even numbers, single digit numbers) and match the captured image with the group of numbers. This process may be iterative and may be performed until there is convergence to a matched, correct presorted image or to a subgroup of prestored images.

Figure 4A:
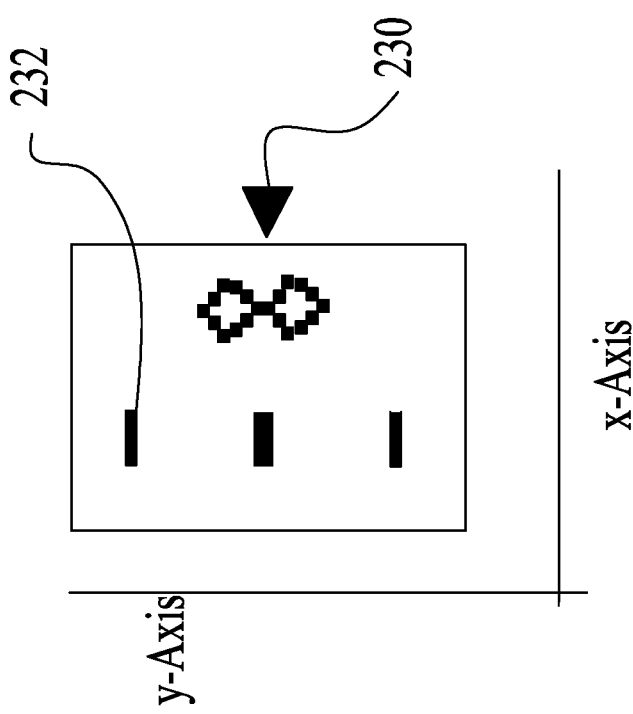

For example, in the case the captured image is as shown in FIG. 4A, initially the image classification process may be configured to identify the parity of the captured image and the presorted images. In this example, the captured image is an even number "8". Accordingly the image processor 192 and/or classifier 202 is configured to further perform the image classification process on the subgroup of prestored images containing even numerals. Thereafter the image classification process may be configured to identify the number of digits of the captured image and the presorted images.

In this example, the captured image contains a single digit "8". Notably, now a subgroup of five potential prestored images remain containing "0", "2", "4", "6" and "8". Accordingly the image processor 192 and/or classifier 202 is configured to further perform the image classification process on the remaining subgroup in any suitable manner, such as by comparing the black pixel density distribution of the captured image with the subgroup of the prestored images until the captured image "8" is matched with the correct prestored image "8". This exemplifies the performance of the image identification procedure by the image classification process, which may be performed in some embodiments, in an iterative, converging process.

Figure 4D:
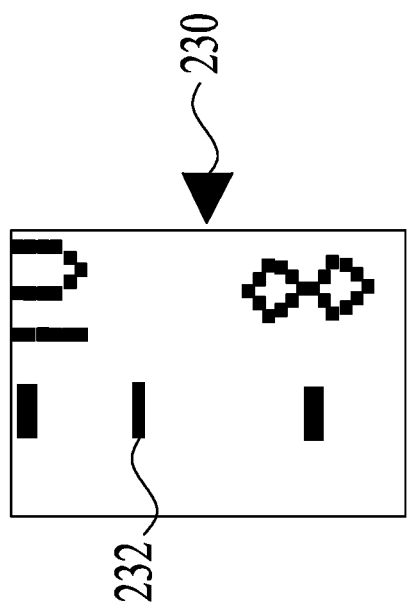
Figure 4F:
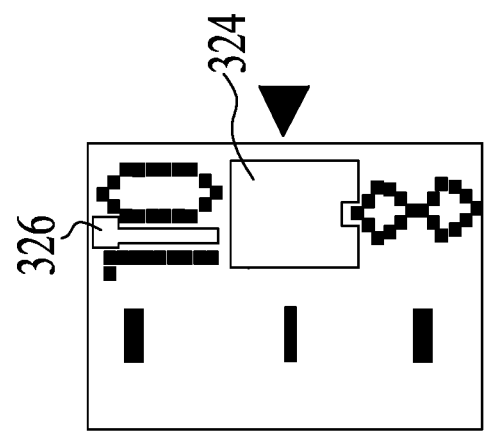

In some embodiments, the predetermined value may comprise the spatial distribution of the white (or black) pixels on the image. As seen in FIG. 4F, the processor 180 may be configured to identify white pixel areas on the image, such as area 324 intermediate two numbers and/or area 326 intermediate the digits of the same number or at any other space on the image. The spatial distribution of the white areas on the image can differentiate a particular image from the other images. Accordingly, the image processor 192 and/or classifier 202 may be configured to compare, and accordingly match, the white-pixel area spatial distribution of the captured image with the prestored image.

Figure 3C:
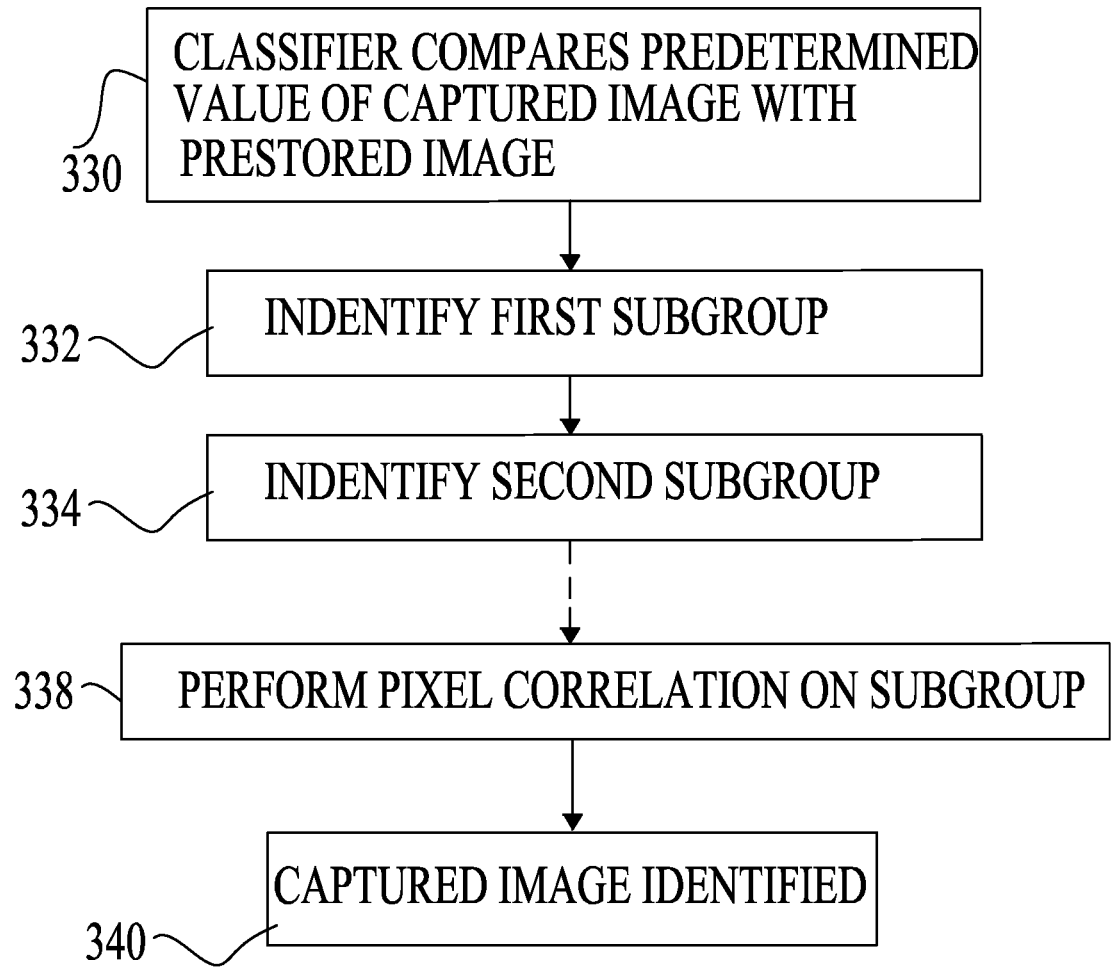

According to some embodiments, the image classification process may be deployed by a combination of the above-mentioned processes, as shown in the flowchart of FIG. 3C. At step 330 the image classification process may be performed by first comparing the designated predetermined value of the captured image with the prestored images to converge to a subgroup of the prestored images, as shown at step 332. In some embodiments, the convergence process may be performed one or more times to identify even smaller subgroups of prestored images, as shown at step 334. Once convergence to a desired subgroup is achieved, the correlation process at step 338 may be performed on the remaining, converged subgroup to identify the captured image at step 340.

For example, as described above, following image classification by identifying the parity of the images and thereafter to the order of digits of the image and thus remaining with the converged subgroup of five potential numerals, the image processor 192 and/or classifier 202 may deploy the pixel correlation process to correctly match the captured image with the prestored image. By this combined process, the pixel-to-pixel comparison is performed on a subgroup of five prestored images rather than the full collection of prestored images.

In some embodiments, the predetermined value may be the number of white pixels or any other feature in the image and the white pixel or any other feature distribution on the image. In some embodiments, the predetermined value may be any statistical value ascribed to an image. In some embodiments, the predetermined value may be the mean number of black pixels along the x-axis of the image, or the mean value of black pixels along the y-axis of the image. These averages can provide a graph with mean number of pixels. Additional statistical features can include the location of maximal and/or minimal peaks of black pixels, such as shown in FIGS. 5A and 5B.

According to some embodiments, the image classification process may be deployed by prestoring the predetermined values in an imageless data format, such as an index or a numerical representation, for example.

According to some embodiments, the image classification process may be performed on the entire captured image or on a selected area thereon. For example, the image processor 192 and/or the classifier 202 may be configured to analyze and compare an area surrounding the arrow 230.

Furthermore, processing the image based on the statistical features (i.e. values) and/or pixel correlation allows for identifying the indicia on the image (e.g. numbers, marks 232) even when the image is ambiguous, such as when the dose number is offset from the arrow 230 (FIG. 4D) or when a portion of the window is concealed, such as by dirt.

Performance of the image identification procedure by the image classification process (also referred to as image recognition and/or image comparison) is efficient and accurate.

Figure 4C:
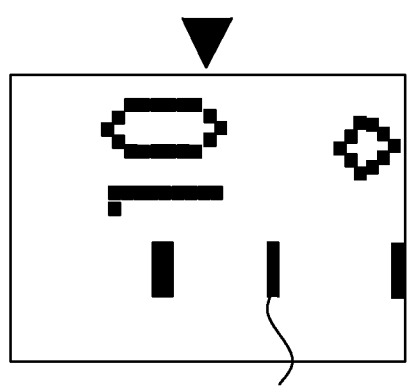
Figure 4E:
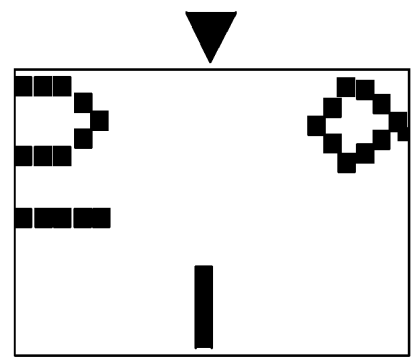

An entirely different process is Optical Character Recognition (OCR). The OCR method is based on translation of the character image (e.g. numbers) into character codes, such as ASCII and is at times performed by a dedicated OCR reader. Since the OCR method comprises translating the characters to known code, the OCR method is susceptible to inaccuracies, particularly when a complex image is captured. Such a complex image may be the image of the window display 130, which may include other features besides alphanumeric characters, such as partial numbers, as shown in FIGS. 4C and 4E, spaces, stray markings, marks 232 and/or dash lines and/or dose arrows 230, or upon offset of the dose number from the dose arrow 230, as shown in FIG. 4D, or if a portion of the image is concealed. Furthermore, in some embodiments the optical sensor 152 may be configured to capture an image comprising a portion of the window 130, so as to decrease the pixel load. This partial image may comprise complete and partial numbers, as shown in FIG. 4E.

In some embodiments, OCR methods may be used by processor 180 alone or in combination with image classification processes.

In some embodiments, the image identification may be performed by the classifier 202 configured to execute other image analysis techniques, such as object recognition, image segmentation, video tracking etc.

In some embodiments, the dose setting detection described at step 304 of FIG. 3A, may be performed by any one or more signals, such as a first optical signal, described at step 312, indicating the dose displayed at window 130 and a second optical signal containing the scale and/or numerical markings 124, for example.

Back to FIG. 3A, in some embodiments, the event of injection of the selected dose may be detected, as shown at step 344, in any suitable manner and sequence.

For example, as shown at step 346, clicks, or any other sound or movement, generated by advancement of the piston 118 (or movement within the shaft 108) while injecting the dose, may be detected by the vibration sensor 154 and/or the auditory sensor 156.

In many injection devices 106, the injection of the dose returns the display at window 130 to "0", namely to an initial pre-set state. Following the vibration or auditory detection of the dose setting, the processor 180 may be configured to activate the optical sensor 152, such as the camera 161, for capturing the image of the selected dose displayed in the window 130, as shown at step 347.

When the captured image is detected as comprising the display of the "0" (or an initial pre-setting state) the processor 180 may be configured to identify the drug dose as being injected. At step 348 the memory module 206 is configured to store the detected dose for tracking the delivered drug dose.

It has been found that in some injection devices the series of clicks generated during injection may be inconstant since the signals are affected by the state of the injection device 106 and/or tracking device 102 and background vibrations and noises. For example, as more drug units are injected and use of the injection device 106 progresses, the amplitude of the injection clicks weakens. Furthermore, it may be difficult to distinct between each click signal of the click series. Moreover, should the coupling of the tracking device 102 with the injection device 106 loosen, such as due to use, the detected injection click signal may weaken.

Figure 3D:
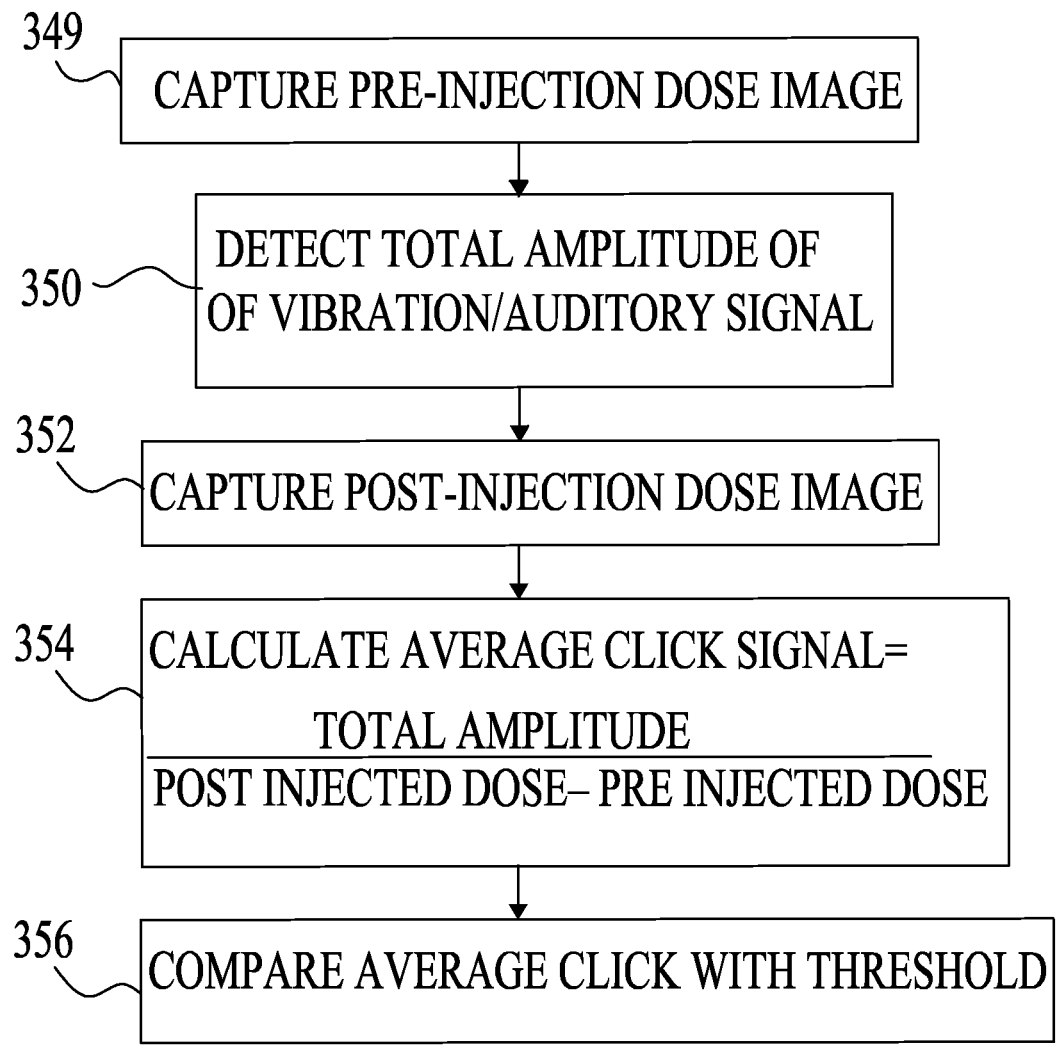

To ensure correct detection of an injection event, in some embodiments, the detection of the injection event at step 344 may be performed according to the steps of FIG. 3D.

At step 349 the optical sensor 152 may capture the dose image of the window 130, prior to injection or may retrieve the pre-injection dose image from memory module 206. The image may be identified according to the image classification process of step 312 or any other image identification method.

At step 350 the processor 180 may be configured to detect the total amplitude (also referred to as "energy level" or vibration or auditory pressure) of the vibration or auditory signal generated during injection. The detection may be performed by the vibration sensor 154 or the auditory sensor 156.

At step 352 optical sensor 152 may capture the dose image of the window 130, following the injection. The post-injection dose image may be identified according to the image classification process of step 312 or any other image analysis method.

At step 354 the processor 180 may be configured to calculate an average click signal by dividing the total amplitude of step 350 by the difference between the post-injection dose image captured at step 352 and the pre-injection dose image captured at step 349.

At step 356 the calculated average click is compared by the processor 180 (or a signal comparison module) to a predetermined amplitude threshold. The predetermined amplitude threshold may be determined by an amplitude provided by the injection device manufacturer, or by prerecording an injection click following manufacture of the injection device and prior to use (typically under ideal, noiseless conditions) or by signaling the user to perform a calibration injection during the calibration step 301 (FIG. 3A) or by any other method. The injection clicks may be recorded at different states of the injection device 106, such as containing the full volume of the drug, a partial volume of the drug, a half full volume of the drug, and/or empty.

Should the calculated average click match the predetermined amplitude threshold, the injection event is detected as in step 344 (FIG. 3A) and may be stored at step 348. If a mismatch is found, the detected clicks may be identified as having been performed during irregular use, as will further be described at step 358.

The method of FIG. 3D, in some embodiments, may be utilized for identifying the setting click. At step 349 the pre-setting image may be captured. At step 350 the total amplitude of the setting clicks may be detected. At step 352 the post-setting image may be captured. At step 354 the average click signal may be calculated by dividing the total amplitude of step 350 by the difference between the post-setting and pre-setting dose of respective steps 352 and 349. At step 356 the calculated average setting click is compared by the processor 180 (or a signal comparison module) to a predetermined amplitude threshold, which may be a prerecorded setting click or any other suitable threshold value. Should the calculated average click match the predetermined amplitude threshold, the dose setting is detected as in step 304 (FIG. 3A).

In some embodiments, the method of FIG. 3D may be utilized for distinguishing between the setting click and the injection click. At step 349 the pre-injection (or pre-setting) dose image may be captured. At step 350 the total amplitude of the clicks may be detected. At step 352 the post-injection (or post-setting) dose image may be captured. At step 354 the average click signal may be calculated by dividing the total amplitude of step 350 by the difference between the post-injection (or post-setting) and pre-injection dose (or pre-setting dose) of respective steps 352 and 349. At step 356 the calculated average setting click is compared by the processor 180 (or a signal comparison module) to a predetermined amplitude threshold. The predetermined amplitude threshold in this embodiment demarcates the injection click, which amplitude is lower than the threshold, from the setting click, which amplitude is higher than the threshold. In a non limiting example, the predetermined amplitude threshold may be 2 g, the injection clicks may be in a range of 0.5-2 g and the setting clicks may be in a range of 2-4 g.

It is noted that in some embodiments, the injection event detection of step 344 may be performed by a single step, such as only by detection of the sound or movement, generated during injection as described at step 346 or only by detection of the image as described at step 347. In some embodiments, a method for detecting the injection event at step 344 comprises detecting the series of clicks generated during injection and enumerating the clicks.

In some embodiments, following step 348, the processor 180 may be configured to identify a static state of the tracking device 102, such as by imaging the display remaining on zero "0" for a predetermined time span and/or no vibration or auditory signals for a predetermined time span. Should the static state be identified, the tracking device 102 may reenter into the standby or low energy mode prior to re-activation at step 302.

Turning to step 358, it was found that during injection of the drug dose the injection device 106 may be subjected to intentional or unintentional misuse or irregular use resulting in different scenarios of dose setting and/or injection. To prevent false detection of a dose injection or detection of an incorrect dose or failure to detect an injected dose, the processor 180 may be configured to distinguish between various scenarios of correct use and misuse, some scenarios are described as follows:

(i) a first injecting scenario when a dose is set and injected into the user.

(ii) a second priming scenario when a small dose, e.g. of 1 or 2 units is set and injected into the air as a prime shot to release air bubbles trapped in the injection device 106.

(iii) a third early setting scenario, when the dose is set, yet not injected.

(iv) a fourth inadvertent scenario, when the dose is inadvertently set and may even possibly be unintentionally injected into the air.

(v) a fifth scenario where the dose is intentionally set, yet only partially injected.

(vi) a sixth scenario where the user inadvertently sets the dose at a partial unit, such that the selected dose is offset from dose arrow 230, as shown in FIG. 4D.

Distinguishing between the different scenarios may be performed at step 358 by the processor 180 according to a predetermined series of rules and instructions. For example, by checking the volume of the set dose (i.e. is the dose less or more than a few units) and/or occurrence of an activity (i.e. another injection) following a passage of a predetermined time span (measured by timer 210) after a first injection or dose setting.

For example, to distinguish between the first injecting scenario and the second priming scenario, the processor 180 may be configured to detect consecutive injections. For example, an injected dose may be detected to be a few units, and an additional consecutive injection is detected within a set time frame thereafter. The set time frame may be partial seconds, a few seconds, less than five seconds, less than ten seconds, less than twenty seconds, less than thirty seconds, less than a minute thereafter, or less than five minutes thereafter—e.g. a range of 0.1 seconds to 60 seconds and subranges thereof, or a few minutes. If a consecutive injection is detected, the first injection may be stored in the memory module 206 as a prime shot and the consecutive injected dose will be stored as the actual injected dose. If occurrence of a consecutive injection is not detected, the first injection may be stored in the memory module 206 as the actual injected dose.

In another example, the processor 180 may be configured to distinguish between the first injecting scenario, when the set dose is immediately injected by the user, and the third early setting scenario, when the dose is set, yet will be injected in the future, such as after a passage of a relatively long time (e.g. longer than a predetermined time span, e.g. a seconds, milliseconds or minutes). Thus, in a case of passage of more than the predetermined time span after a dose setting, the processor 180 may be configured to store the detected set dose in the memory module 206 as an anticipated dose to be injected in the future. Upon the occurrence of the future injection, (detected by the processor 180) the stored set dose may be stored by the memory module 206 as an actual injected dose.

In another example, the processor 180 may be configured to distinguish between the first injecting scenario, when the dose is injected into the user and the fourth inadvertent scenario when the set dose may be inadvertently injected into the air or inadvertently set as a result of fiddling with the injection pen or any other irregularity. For example, the processor 180 may be configured to detect an occurrence of an additional consecutive injection within a few seconds, milliseconds or minutes. Assuming that a user will not voluntarily inject himself repeatedly within a short time frame, if a consecutive injection is detected, the first injection may be stored in the memory module 206 as an inadvertent setting or injection or may not be stored at all. The consecutive injected dose will be stored as the actual injected dose. If occurrence of a consecutive injection is not detected, the injection may be stored in the memory module 206 as the actual injected dose.

In yet another example, the processor 180 may be configured to distinguish between the first injecting scenario and the fourth inadvertent scenario, when the knob 120 was inadvertently rotated and then returned (e.g. intentionally) to its initial state "0" without an occurrence of an injection. For example, the processor 180 may be configured to expect detection of an injection occurrence (detected by the vibration sensor 154 and/or the auditory sensor 156 of step 346) between the detected images set dose of step 312 and the detected image containing the return to the initial state to "0" of step 347. Should the absence of the injection be detected, the dose setting may be stored in the memory module 206 as an inadvertent setting or may not be stored at all. This example demonstrates the advantage of detecting the injected dose by two different types of signals, the optical signal, detecting the window image, and the vibration or auditory signal, detecting the injection occurrence.

In a further example, the processor 180 may be configured to distinguish between the first injecting scenario and the fifth scenario, when the knob 120 was intentionally rotated yet the dose was only partially injected. For example, the processor 180 may be configured to compare the detected imaged dose, prior to injection, with the detected imaged dose, following injection, and subtract the later imaged dose from the earlier imaged dose. In another example, the processor 180 may be configured to compare the detected imaged dose prior to injection with the number of clicks detected during injection and accordingly determine the actual injected dose.

In another example, the processor 180 may be configured to correctly detect the sixth scenario where the user inadvertently sets the dose at a partial unit, such that the selected dose is offset from dose arrow 230. In some injection devices 106 partial unit setting will result in either a smaller whole unit injection or a larger whole unit injection. For example, as shown in FIG. 4D, the injected dose may be either 8 units or 9 units. This ambiguity may be resolved by determining the dose according to the number of clicks detected by the vibration or auditory signals at step 306.

It is appreciated that many different scenarios, intentional or unintentional, may occur during use of the injection device 106 and the tracking device 102 may be configured to consider these scenarios to correctly track the injected dose.

In some embodiments, the different scenarios may be identified by use of the tracking device 102 in combination with an Application running on the external device 176. The Application may be programmed to consider the different scenarios described above and accordingly identify the actual, correct scenario.

In some embodiments, the user may be requested to confirm or correct the actual injected dose.

The injection device 106 and the sensors 150 may be subjected to disturbances interfering with the correct detection of the dose setting and/or injection. These disturbances may include, for example, inadvertent movement of the injection pen 106, which may interfere with the vibration sensor 154; background noises, which may interfere with the auditory sensor 156; rapid rotation of the knob 120 during setting, which may interfere with the vibration sensor 154 and/or the auditory sensor 156; rapid injection of the injection device 106, which may interfere with the vibration sensor 154 and/or the auditory sensor 156; glaring light on the dose window 130, or insufficient lighting, which may interfere with the optical sensor 152.

Detection by at least two signals may enhance the precision of the tracking device 102. In various embodiments, the at least two signals can be different types of signals, such as vibration and optical; or the same type of signal, each signal indicative of different information, e.g. the optical sensor detecting the dose displayed at window 130 and the optical sensor detecting the position of the piston 118; the same type of signal, each indicative of different information, e.g. the optical sensor 152 detects the image displayed at the window 130 and the optical sensor 152 tracking the x-axis and/or y-axis shift of the surface inside the window 130; or even the same type of signal indicative of the same information, e.g. the optical sensor detecting the dose displayed at window 130 within a very short time span, such as within a few seconds or milliseconds. For example, when one signal is unclear or fails to be detected, the other signal may be used. Furthermore, the different signals may be used to distinguish between various setting and/or injecting scenarios, as described at step 358.

It is further noted that in some embodiments, a first signal may be used to awaken and activate an otherwise second (same or different) dormant sensor to generate a second signal indicative of the set dose and/or injection.

In some embodiments, the processor 180 may be configured to manage the different detected signals in a case wherein a discrepancy arises between the detected doses. In a non-limiting example, upon a discrepancy arising between the dose detected by the vibration sensor 154 at step 306 and the dose detected by the optical sensor 150 at step 312, the processor 180 is configured to select the dose detected by the optical sensor 150 and store it as the accurate set dose in the memory module 206.

In some embodiments, the two (or more) signals may be used wherein one of the signals is unclear, such as wherein the captured image is ambiguous or classification of the image is converged to two similar options, e.g. to the number "12" and "21", the processor 180 may be configured to consider the dose detected by the clicks at step 306, to determine the correct image, and hence the correct dose. Another example for ambiguity was described in reference to the sixth scenario at step 358. The correct dose may be stored in the memory module 206.

In some embodiments, the two (or more) signals may be used to optimize the image identification procedure. The image classification process may be configured to identify a single image or a subgroup of images that match the detected clicks. The pixel-to-pixel comparison may be performed on a single prestored image or a subgroup of prestored images, rather than the full collection of prestored images.

In some embodiments the injected dose may be detected by other methods than described herein in reference to steps 300 to 358 (FIGS. 3A-3D) or may be detected in combination with these steps. For example, the detected injected dose can be verified by detecting the volume of drug remaining in the injection device 106, following injection. This may be performed in any suitable manner, such as by prompting the user to enter the injected dose into the Application or any other user interface. The Application and/or processor 180 may be configured to retrieve the drug dose injection history from memory module 206 to calculate the total volume of injected drug since commencement of use of the drug, based on the injection history and the currently entered dose. The remaining volume of drug may be calculated by subtracting the volume of injected drug from the original volume of drug contained within the injection device 106.

In some embodiments, the volume of drug remaining in the injection device 106 may be calculated by the processor 180 based on the amplitude of the clicks generated during injection. In some injection devices 106 during initial use thereof, the amplitude of the clicks generated during injection is relatively high. As more drug units are injected and use of the injection device 106 progresses, the amplitude of the clicks weakens. Accordingly, the memory module 206 may store a scale correlating between a detected click amplitude and a remaining volume of drug in the injection device 106. The scale may be based on empirical data. In some embodiments, the empirical data may be gathered by prerecording clicks generated by injection devices 106 with varying volumes of drug therein. (This empirical data may be used to perform the calibration step 301.)

It is noted that in some embodiments, the dose setting detection of step 304 may be performed by a single step, such as only by detection of the clicks as described at step 306 or only by detection of the image as described at step 312.

It is appreciated that the processor 180 and its components may be configured with any suitable predetermined sequence of rules and instructions to distinguish between different types of scenarios arising during use of the injection device 106.

It is noted that any one of the steps described in FIGS. 3A-3D may be omitted. The sequence of the steps may be changed.

FIGS. 6-11B illustrate additional embodiments of a tracking device 102.

Figure 6:
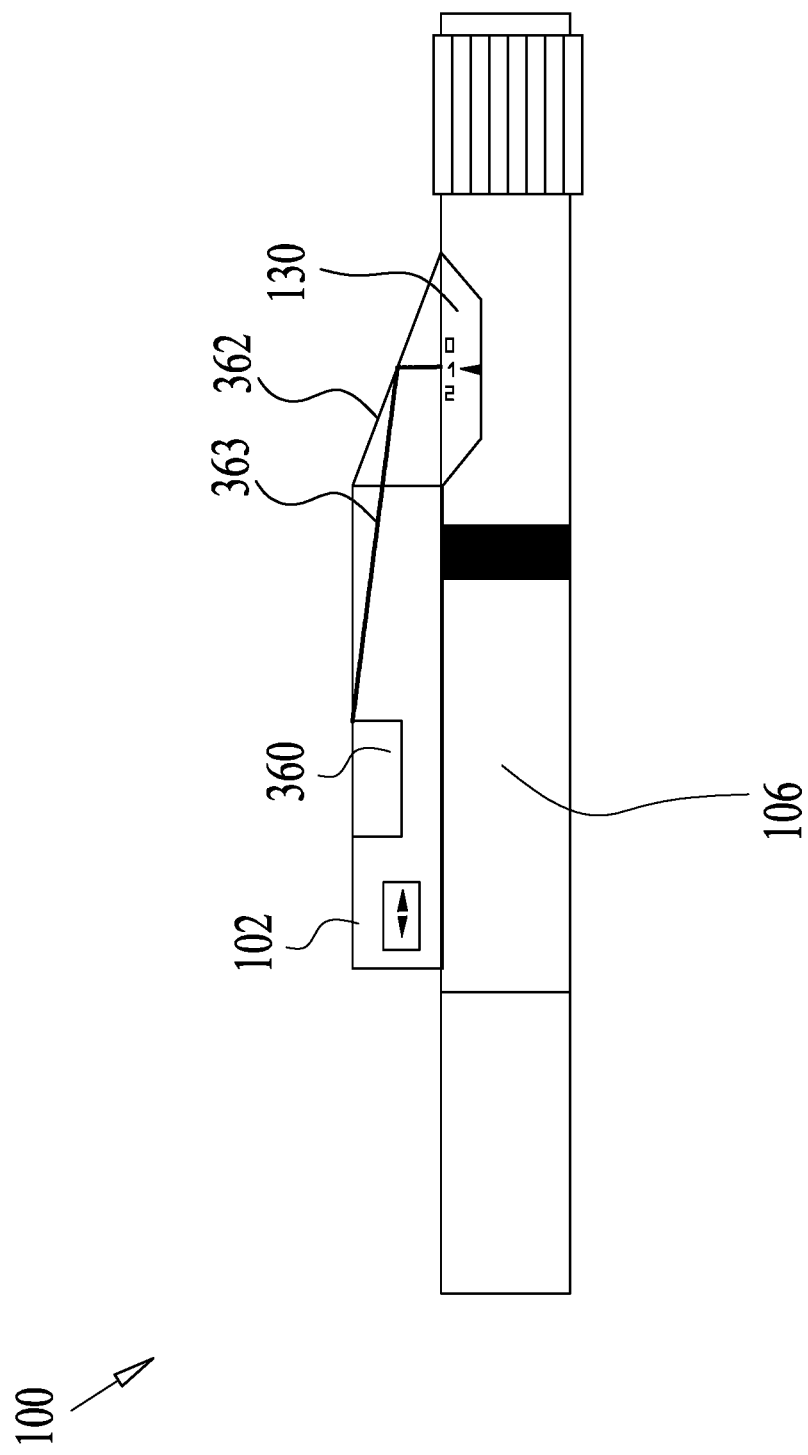
FIG. 6 is a schematic illustration of an exemplary drug dispensing-tracking system, constructed and operative according to some embodiments of the present disclosure.

As seen in FIG. 6, in some embodiments, the optical sensor 152 may be used. A CCD 360 is placed in a location which allows view of the window 130. An activity trigger may be utilized to activate the CCD 360 which videos the window changes. The tracking device 102 may be formed with an incline 362 (e.g. 45°) operating as a "prism" so that the display window 130 can be seen from above without the CCD 360 blocking it from the user's eye, as illustrated by line 363.

Figure 7:
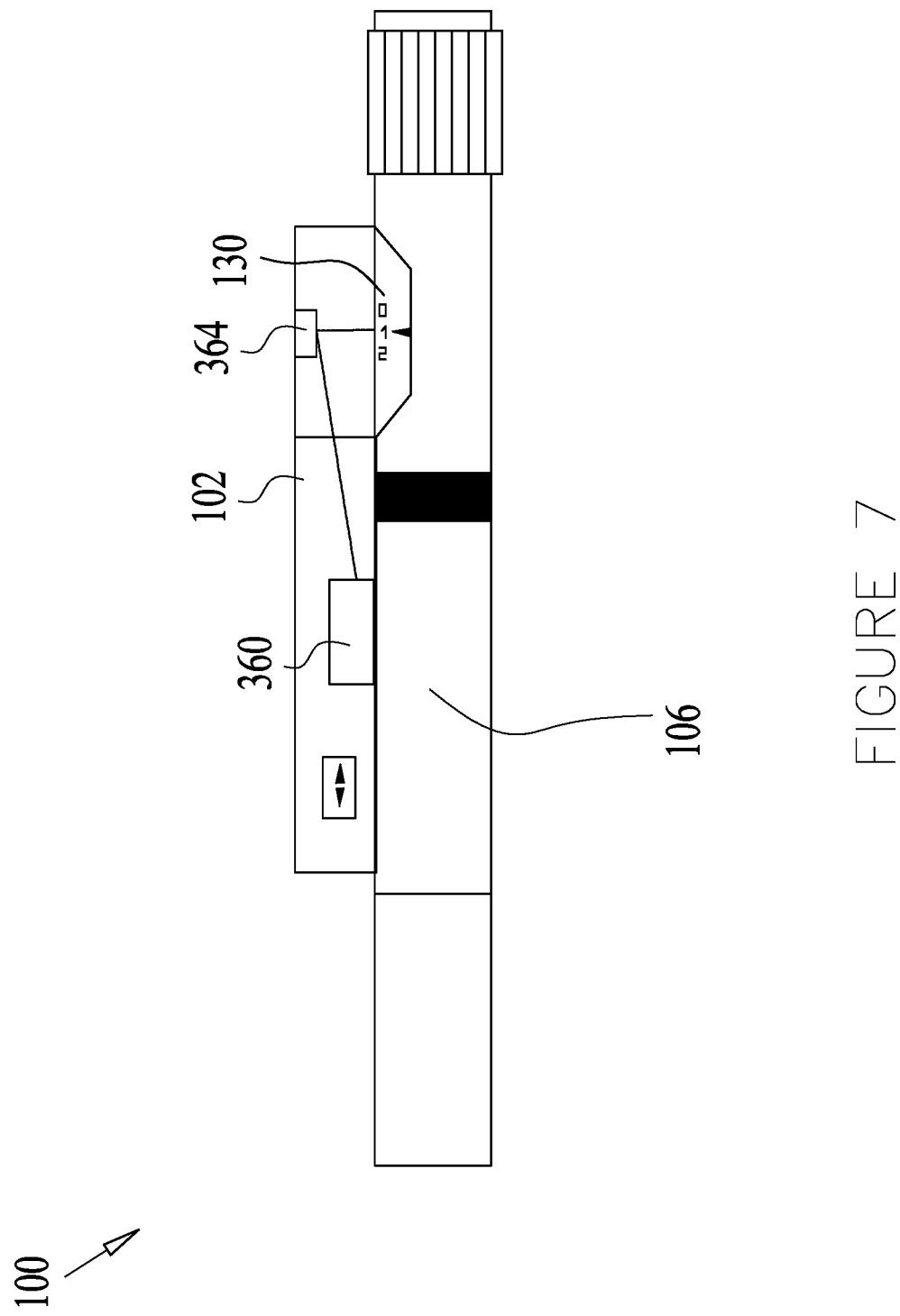
FIG. 7 is a schematic illustration of an exemplary drug dispensing-tracking system, constructed and operative according to some embodiments of the present disclosure.

In some embodiments, as seen in FIG. 7, the tracking device 102 may comprise a mirror 364 placed in alignment with the display window 130 and configured to reflect the display image to the CCD 360. Alternatively, the mirror 364 may be placed at an angle relative to the display window 130 configured to reflect the display image to the CCD 360.

In some embodiments, the optical sensor 152 may capture "still" images. In some embodiments the optical sensor 152 may capture a video. The optical sensor 152 may be configured to identify the indicia displayed on the display window 130.

In some embodiments, the indicia my comprise a barcode image. The barcode image of the injection device 106 may be imaged by the optical sensor 152. The barcode may encode data related to the type of injection device and/or drug or the manufacturing and expiration date of the injection device 106, for example.

Figure 8:
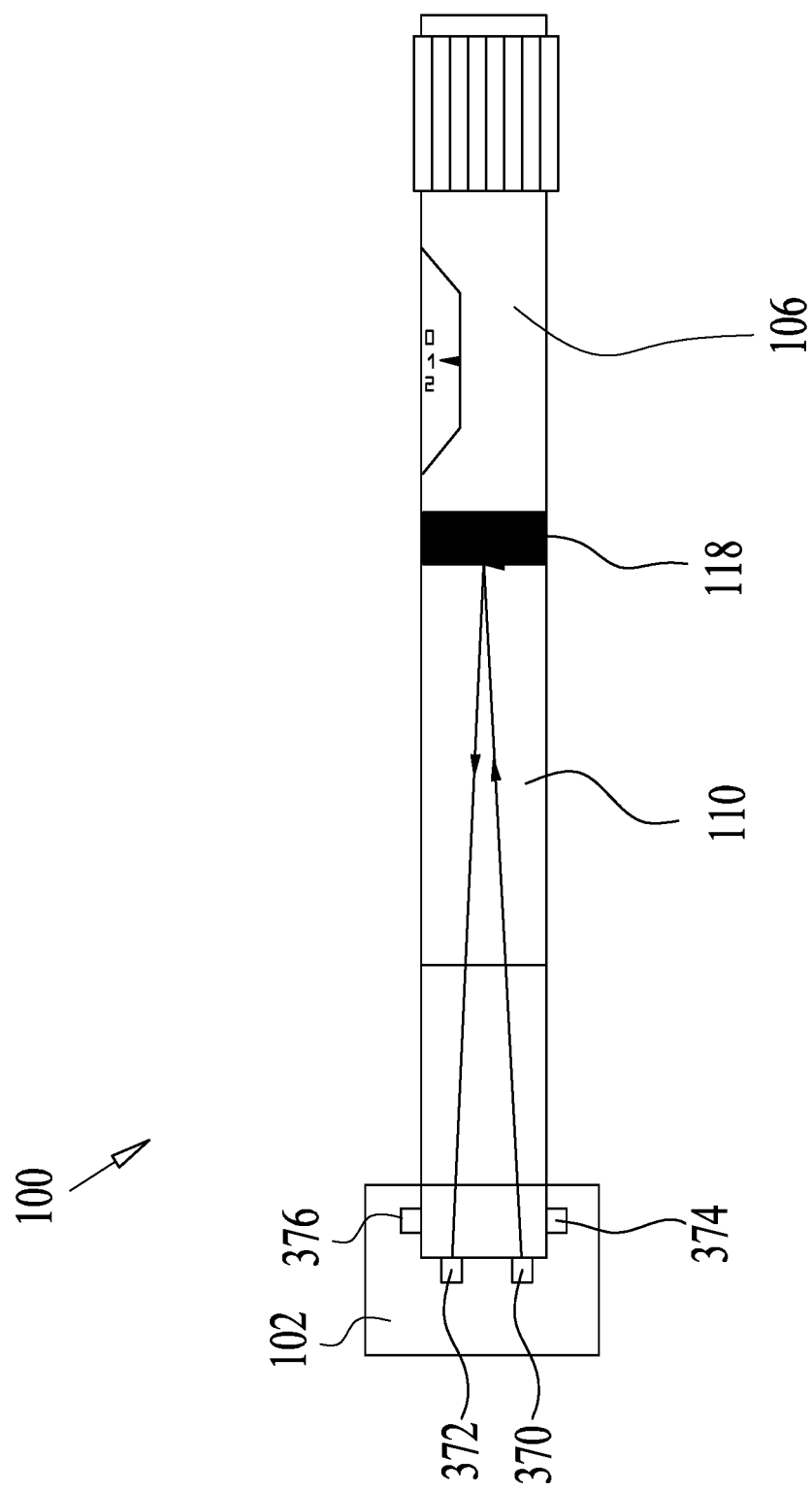
FIG. 8 is a schematic illustration of an exemplary drug dispensing-tracking system, constructed and operative according to some embodiments of the present disclosure.

As seen in FIG. 8, in some embodiments the tracking device 102 may comprise the acoustic (i.e. auditory) sensor 156 configured for detecting an acoustic signal traveling inside the injection device 106 and thus determine the amount of fluid in the reservoir 110.

An acoustic source 370 may generate an acoustical impulse signal and/or a continuous signal which travels to the piston 118 through the drug fluid medium. The returning signal is detected by detector 372. The signals detected by the detector 372 are composed of sound traveling through the plastic which should have a fixed delay time and should be the fastest signal and would mark the time as zero. Signals reflecting from the piston 118 arrive later and the time delay is proportional to the distance from the piston 118 to the source 370 and detector 372.

A temperature sensor may be provided to measure the drug fluid medium. Alternatively, since the velocity of sound in the fluid medium depends on the temperature, the temperature can be detected by measuring the travel time of sound between the two walls intermediate acoustic detectors 374 and 376. The sound source 370 may comprise any suitable means such as a piezoelectric source or an ultrasonic source, for example. The detectors 372, 374 and 376 may comprise any suitable means, such as a microphone.

FIGS. 9A-9C are a schematic illustration of an exemplary drug dispensing-tracking system 100 at three operational stages constructed and operative according to some embodiments of the present disclosure. As seen in FIGS. 9A-9C, as the rotation knob 120 is turned to set the dose, the inner cylinder 128 elongates as the dose is increased, as seen by comparing FIG. 9A with FIG. 9B. Likewise, the inner cylinder 128 shortens as the dose is decreased or following injection, as seen by comparing FIG. 9B with FIG. 9C. The single or plurality of sensors 150 may be configured to detect the displacement of the inner cylinder 128. The displacement, which can be measured in millimeters for example, may correspond to an increase in dose units. The processor 180 may be configured to convert the displacement to the selected dose units. Likewise, as the rotation knob 120 is turned to decrease the dose, the single or plurality of sensors 150 may detect the displacement and the processor 180 is configured to convert the displacement to the decreased dose units.

As the dose is injected the amount of drug in the reservoir 110 decreased as indicated by the displacement of the piston 118 as seen by comparing FIG. 9A with FIG. 9C. In some embodiments, the single or plurality of sensors 150 may be configured to detect the displacement of the piston 118. The single or plurality of sensors 150 may comprise the optical sensor 152 which may capture an image of the piston 118 before and after displacement. Additionally or alternatively the scale markings 124 may be captured before and after the dose injection and the processor 180 is configured to calculate the injected dose from the position of the piston 118 or drug relative to the scale markings 124.

The single or plurality of sensors 150 may comprise the vibration sensor 154, a movement sensor or any other displacement sensor for detecting the displacement of the piston 118.

Turning to FIG. 10, the displacement of the inner cylinder 128 may be measured by an array of magnetic sensors 380, such as Hall Effect sensors which are operative to measure movement and can be indicative of the displacement in the display window 130 and/or of the of the inner cylinder 128 and/or of piston 118.

As seen in FIGS. 11A and 11B, the displacement of the inner cylinder 128 may be detected by any suitable type of indicia. In some embodiments, each revolution of the rotation knob 120 may be marked by rings 382 of different colors or other distinction. The single or plurality of sensors 150, such as an optical sensor 152, may detect the ring color. The processor 180 may be configured to determine the displacement of the inner cylinder 128 according to the detected ring(s). The processor 180 may employ image classification methods for matching the captured image with a prestored image, such as an image comprising one or more ring colors.

In some embodiments, such as any one of the embodiments of FIGS. 1A-11B, the tracking device 102 is embedded in the cap of the injection device 106. In some embodiments, the measurement of dosage is activated upon opening and closing the cap.

In some embodiments whereupon the tracking device 102 is embedded in the cap, the tracking is based on measurement of changes in the volume of fluid left in the injection device cartridge occurring between opening and closing of the cap.

In some embodiments, commercial injection devices 106 are designed by each manufacturer usually with unique mechanical features. As described, the tracking device 102 may be formed with mechanical features corresponding to the unique mechanical features of a selected commercial injection device and may be non-interchangeable with another tracking device formed with mechanical features corresponding to the unique mechanical features of another selected commercial injection device. Accordingly, each tracking device 102 may be identified by its mechanical features and may be associated with a selected commercial injection device. Each type of a commercial injection device 106 may be configured to inject a specific type of drug and a specific dose. Therefore, in identifying the corresponding tracking device 102, the specific type of drug and a specific dose may also be identified.

In some embodiments, the tracking device 102 may be formed with attachment means configured to fit with various commercial injection devices.

In some embodiments, the type of commercial injection device 106 may be identified by imaging the injection device 106, which may distinguishable from other commercial injection devices by the color of the cap or other structural feature, a different shape or form of the cap or other feature.

In some embodiments, operation of the tracking device 102 may be automatic without user intervention. In some embodiments, some or all activities of the tracking device 102 may be initiated by the user such as by pressing a control button 400 (FIG. 1C). In some embodiments, the button 400 may be used to commence operation of the tracking device 102. In some embodiments, the button 400 may be used for the user to verify the detected drug dose. For example, the user may set the drug dose and push the button 400. Once the button is pushed, the processor 180 activates the optical sensor 152 to take an image of display window 130, determine the set drug dose, and store the set drug dose in the memory module 206. In some embodiments, the dose is detected without user intervention or verification.

In some embodiments, the injection device 106 may be provided with usability features. For example, a feature may include identifying the location of the injection device 106. In a non-limiting example, the injection device 106 may be located by using the Bluetooth functionality on a management Application (running on the external device 176) of the injection device 106 to find its location such as by using the "FindMe" and "proximity" profiles of a Bluetooth low energy (BLE) protocol.

In some embodiments, the temperature of the injection site and/or the drug may be sampled intermittently (e.g. every 1 minute) with accuracy level of at least±0.5° C., in a non-limiting example.

In some embodiments the achieved accuracy using the methods and tracking device 102 described herein is relatively high such as within the limits of 10% (±1 IU) for 10 IU and 5% (±1.5 IU) for 30 IU or an accuracy of 0.5 unit or less.

In some embodiments, the Application may include a feature capable of receiving input from the tracking device 102. In some embodiments, the Application may receive input from a plurality of drug delivery devices (including non-injected drugs, such as oral delivery), each delivering the same or different drug. The effect of each drug of the user's blood glucose level or any other analyte and/or the total accumulative effect may be displayed numerically, graphically or in any other method.

Such a plurality of drugs may include at least one or more of: basal insulin, bolus insulin, meal insulin, long acting insulin, rapid acting insulin, a mix of insulin, Dipeptidyl peptidase-4 (DPP-4, Gliptins) drugs, commercially available as Januvia®, glucagon-like peptide-1 (GLP-1) drugs commercially available as Victoza®; and any other drug, typically drugs affecting the body glucose level.

The drug my include any pharmaceutical formulation containing at least one pharmaceutically active compound delivered in any form, e.g. liquid, gel, gas and powder, for example.

In some embodiments, the image processor 192 may be configured to perform image processing on the captured image such as division by a previously captured background image; binning of the image to reduce the number of pixels for further evaluations; normalization of the image to reduce intensity variations in the illumination; sheering of the image; and/or binarization of the image by comparing to a fixed threshold.

It is noted that the terms acoustic, sound, audio and auditory are used interchangeably herein.

Further embodiments of tracking devices and their components may be used, engaged or embedded in the tracking device 102 are described in applicant's PCT publication WO2014/064691 and PCT publication WO2016/071912, each of which is incorporated herein by reference in their entireties.

In some embodiments, the external device 176 may comprise a treatment device worn on the skin of a user to treat an injection site to improve the pharmacodynamics or pharmacokinetics of the drug. The injection site may be an intradermal layer. The treatment device may comprise a treatment device, such as INSUPAD®, disclosed in Applicant's PCT patent applications WO/2008/114218, WO/2010/052579, and/or WO/2012/153295, each of which is incorporated herein by reference in their entireties.

In some embodiments, the external device 176 may comprise an analyte sensor configured to measure an analyte level in the body, such as a blood glucose meter, for example. In some embodiments, external device 176 may comprise an activity level sensor, e.g. a pedometer, operative to measure the activity level of the user. In some embodiments, the external device 176 may comprise a physiological function sensor operative to measure any physiological function of the body, such as a blood pressure meter or pulse meter, for example.

In some embodiments, the processor 180 may comprise a microprocessor, a Digital Signal Processor (DSP), Application Specific Integrated Circuit (ASIC), Field Programmable Gate Array (FPGA) or the like. Processor 180 may executes program code (e.g. software or firmware) stored in a program memory, such as the memory module 206, to store intermediate results. Memory module 206 may be used, inter alia, to store history of prior use, doses, injection, times, or any other related data. Memory module 206 may comprise for example, Read-Only Memory (ROM), a Random Access Memory (RAM), and/or tangible storage medium or any suitable storage medium.

In some embodiments, the processor 180 may be configured to instruct the memory module 206 to erase a prior stored injected drug dose image with a more recent injected drug dose. The processor 180 may be configured to compare at least one indicia of the drug dose in the captured image with the pre-stored indicia of a most recent stored injected drug dose and successive pre-stored indicia of drug doses.

In some embodiments, there is provided method for determining an injected drug dose from the injection device 106, by capturing, via the optical sensor 152 configured to capture images through the window 130, a plurality of calibration images of a dose ring 128 of the injection device 106; detecting, via a sensor 150, at least one click signal generated by setting the set drug dose on the injection device 106; capturing, via the optical sensor 152, an image of dosage markings on the dose ring 128 before the injection device injects 106 a drug; detecting, via the sensor 150, at least one click signal generated by injecting the set drug dose; comparing, via processor 180, the image to the plurality of calibration images to determine the injected drug dose.

In some embodiments, the method may further comprise storing, at the memory 206, the matched one of the plurality of calibration images; detecting, via the sensor 150, at least a second click signal generated by setting a second set drug dose on the injection device 106; capturing, via the optical sensor 152, a second image of dosage markings on the dose ring 128 before the injection device injects a second amount of drug; detecting, via the sensor, at least one second click signal generated by injecting the second set drug dose; comparing, via the processor, the second image to subsequent images from the plurality of calibration images, the subsequent images from the plurality of calibration images having higher doses compared to the matched one of the plurality of calibration images; and determining, via the processor 180, the second injected drug dose when features of the second image match features of one of the subsequent images from the plurality of calibration images.

Various implementations of some of embodiments disclosed, in particular at least some of the processes discussed (or portions thereof), may be realized in digital electronic circuitry, integrated circuitry, specially configured ASICs (application specific integrated circuits), computer hardware, firmware, software, and/or combinations thereof. These various implementations, such as associated with the drug dispensing-tracking system 100 and the components thereof, for example, may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions/code for a programmable processor, for example, and may be implemented in a high-level procedural and/or object-oriented programming language, and/or in assembly/machine language. As used herein, the term "machine-readable medium" refers to any computer program product, apparatus and/or device (e.g., non-transitory mediums including, for example, magnetic discs, optical disks, flash memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on the external device 176 may comprise a computer having a display device (e.g., a LCD (liquid crystal display) monitor and the like) for displaying information to the user and a keyboard and/or a pointing device (e.g., a mouse or a trackball, touchscreen) by which the user may provide input to the computer, a remote control, PC, laptop, smartphone, media player or personal data assistant ("PDA"). Other kinds of devices may be used to provide for interaction with a user as well. For example, feedback provided to the user may be any form of sensory feedback (e.g., visual feedback, auditory feedback, or tactile feedback), and input from the user may be received in any form, including acoustic, speech, or tactile input. Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components.

The components of the system may be interconnected by any form or medium of digital data communication (e.g., a communication network). Examples of communication networks include a local area network ("LAN"), a wide area network ("WAN"), and the Internet. The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety.

Example embodiments of the devices, systems and methods have been described herein. As may be noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements/features from any other disclosed methods, systems, and devices, including any and all features corresponding to translocation control. In other words, features from one and/or another disclosed embodiment may be interchangeable with features from other disclosed embodiments, which, in turn, correspond to yet other embodiments. Furthermore, one or more features/elements of disclosed embodiments may be removed and still result in patentable subject matter (and thus, resulting in yet more embodiments of the subject disclosure).

The invention claimed is:

1. A drug tracking device used in combination with a drug injection device configured to display indicia of drug doses comprising at least a portion of one or more numbers from a range of numbers running from a minimal to a maximum number of drug units, corresponding to the volume of deliverable dose units contained in the injection device, the drug tracking device comprising:
   a housing configured to engage with the drug injection device;
   an optical sensor configured to capture an image of a portion of the drug injection device, said portion of the drug injection device displaying the indicia of drug doses including at least said portion of one or more numbers, such that a captured image comprises at least one indicia of a drug dose;
   a memory module embedded in the drug tracking device or external thereto, the memory module having pre-stored statistical values corresponding to a spatial distribution of black or white pixels corresponding to said number; and
   a processor having instructions operating thereon configured to identify an injected drug dose via image classification, wherein image classification comprises:
   identifying if said portion of one or more numbers on the captured image belongs to a subgroup of the range of numbers, the subgroup comprising at least:
      odd or even numbers; and
      single or double digit numbers:
   determining a first statistical value, comprising a statistical value corresponding to a spatial distribution of black or white pixels on the captured image; and
   comparing said first statistical value to a second statistical value so as to determine the injected drug dose,
   wherein the second statistical value comprises the pre-stored statistical value, and wherein said second statistical value is selected from the subgroup.

2. The drug tracking device of claim 1, wherein the determined first statistical value and the second statistical value, each comprises at least one of: x-axis distributions of black pixels and y-axis distributions of black pixels.

3. The drug tracking device of claim 1, wherein the determining the first statistical value is performed on a selected area of the captured image.

4. The drug tracking device of claim 1, wherein the determined first statistical value and the second statistical value, each comprises a spatial distribution of areas of white pixels.

5. The drug tracking device of claim 1, further comprising a signal filter comprising an optical element configured to ensure the optical sensor captures a readable image for the processor to compare with the pre-stored statistical values.

6. The drug tracking device of claim 1, further comprising at least one of an auditory sensor, a vibration sensor and a timer,
   wherein the instructions are further configured to cause the processor to distinguish, between at least any two of the following events, based on signals from at least one of the auditory sensor, the vibration sensor, the optical sensor and the timer:
      the injected drug dose is set and injected;
      a small priming dose is set and injected into air;
      the injected drug dose is set and not injected;
      an inadvertent drug dose is set;
      the inadvertent drug dose is set and injected into air;
      the inadvertent drug dose is set and partially injected;
      the inadvertent drug dose is set at a partial unit; and
      a click is generated during setting the drug or injecting the drug.

7. The drug tracking device of claim 1, wherein the drug injection device comprises a display window and the housing is formed with an incline such that the optical sensor is positioned in proximity to the display window, while the display window remains unblocked by the optical sensor.

8. The drug tracking device of claim 1, wherein upon engagement of the drug tracking device with the drug injection device, the optical sensor captures at least one image of the portion of the drug injection device, the memory module further comprises a pre-stored calibration image, and the instructions are further configured to cause the processor to verify alignment of the drug tracking device with the drug injection device by comparing the captured at least one image with the pre-stored calibration image.

9. The drug tracking device of claim 8, wherein the processor is configured to detect a misalignment of the drug tracking device with the drug injection device and further to alert a user of at least one of: a degree of misalignment; and guide the user to correctly position the tracking device on the injection device.

10. The drug tracking device of claim 1, wherein determining the injected drug dose statistical value comprises at least reducing pixel to pixel correlation with the pre-stored statistical value.

11. The drug tracking device of claim 1, further comprising at least one of an auditory sensor and a vibration sensor, wherein the instructions are further configured to cause the processor to:
   determine, based on signals received from the at least one of the auditory sensor and the vibration sensor, that the injected drug dose has been set,
   once the dose has been set, to activate the optical sensor to capture the captured image, and
   determine the injected drug dose.

12. The drug tracking device of claim 1, further comprising at least one of an auditory sensor and a vibration sensor configured for detecting a vibration signal having a vibration amplitude, which is generated by a click signal performed during injection of the injection device,
   wherein the processor is configured for comparing the detected vibration signal with said determined injected drug dose.

13. A method for determining an injected drug dose from an injection device configured to display indicia of drug doses comprising at least a portion of one or more numbers from a range of numbers running from a minimal to a maximum number of drug units, corresponding to the volume of deliverable dose units contained in the injection device, the method comprising:
   capturing an image of a portion of the drug injection device, said portion of the drug injection device displaying indicia of drug doses, including at least said portion of one or more numbers, such that a captured image comprises at least one indicia of a drug dose;
   identifying the injected drug dose via image classification, wherein image classification comprises:
   identifying if said portion of one or more numbers on the captured image belongs to a subgroup of the range of numbers, the subgroup comprising at least:
      odd or even numbers; and
      single or double digit numbers;
   determining a first statistical value, comprising a statistical value corresponding to a spatial distribution of black or white pixels on the captured image; and comparing said first statistical value to a second statistical value so as to determine the injected drug dose,
wherein the second statistical value comprises a pre-stored statistical value corresponding to a spatial distribution of black or white pixels corresponding to said number, and wherein said second statistical value is selected from the subgroup.

14. The method of claim 13, wherein the determined first statistical value and the second statistical value, each comprises at least one of: x-axis distributions of black pixels and y-axis distributions of black pixels.

15. The method of claim 13, wherein the determining the first statistical value is performed on a selected area of the captured image.

16. The method of claim 13, wherein the determined first statistical value and the second statistical value, each comprises a spatial distribution of areas of white pixels.

17. The method of claim 13, further comprising:
providing at least one of an auditory sensor, a vibration sensor and a timer,
wherein the instructions are further configured to cause the processor to distinguish, between at least any two of the following events, based on signals from at least one of the auditory sensor, the vibration sensor, the optical sensor and the timer:
the injected drug dose is set and injected;
a small priming dose is set and injected into air;
the injected drug dose is set and not injected;
an inadvertent drug dose is set;
the inadvertent drug dose is set and injected into air;
the inadvertent drug dose is set and partially injected;
the inadvertent drug dose is set at a partial unit; and
a click is generated during setting the drug or injecting the drug.

18. The method of claim 13, further comprising detecting a misalignment of the drug tracking device with the drug injection device.

* * * * *